United States Patent
Tanaka et al.

(10) Patent No.: US 6,610,710 B2
(45) Date of Patent: Aug. 26, 2003

(54) PHENYLALANINE DERIVATIVES

(75) Inventors: Yasuhiro Tanaka, Kawasaki (JP); Toshihiko Yoshimura, Kawasaki (JP); Chieko Ejima, Kawasaki (JP); Mitsuhiko Kojima, Kawasaki (JP); Eiji Nakanishi, Kawasaki (JP); Hiroyuki Izawa, Kawasaki (JP); Yuko Satake, Kawasaki (JP); Nobuyasu Suzuki, Kawasaki (JP); Manabu Suzuki, Kawasaki (JP); Masahiro Murata, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 10/183,729

(22) Filed: Jun. 28, 2002

(65) Prior Publication Data

US 2003/0114490 A1 Jun. 19, 2003

Related U.S. Application Data

(63) Continuation of application No. PCT/JP00/09223, filed on Dec. 26, 2000.

(30) Foreign Application Priority Data

Dec. 28, 1999 (JP) ............................. 11-374960

(51) Int. Cl.$^7$ .................. A01N 43/40; A01N 37/44; A01N 37/12; A61K 31/445; A61K 31/24
(52) U.S. Cl. .................. 514/330; 546/226; 546/245; 548/127; 560/37; 560/38; 560/39; 560/40; 560/45; 560/47; 562/444; 562/445; 562/446; 562/447; 562/448; 562/449; 562/621; 544/316; 514/331; 514/538; 514/575; 514/561; 514/563; 514/567
(58) Field of Search .................. 544/316; 548/127; 546/189, 190, 191, 218, 226, 245; 562/433, 437, 445, 449, 450, 621, 444, 446, 447, 448; 514/327, 330, 331, 342, 565, 574, 538, 575, 561, 563, 567; 560/37, 38, 39, 40, 45, 47

(56) References Cited

U.S. PATENT DOCUMENTS 6,353,099 B1 * 3/2002 DeLaszlo et al. ........... 540/490

FOREIGN PATENT DOCUMENTS

| WO | WO 98/58902 | 12/1998 |
| WO | WO 99-10312 | 3/1999 |
| WO | WO 00/37429 | 6/2000 |

* cited by examiner

Primary Examiner—Richard L. Raymond
Assistant Examiner—Zachary C. Tucker
(74) Attorney, Agent, or Firm—Oblon, Spivak, McClelland, Maier & Neustadt, P.C.

(57) ABSTRACT

Phenylalanine derivatives of the following formula and analogues thereof have an antagonistic activity to α4β7 integrin and a selectivity toward α4β1 integrin. They are used as therapeutic agents for various diseases to which α4β7 integrin relates.

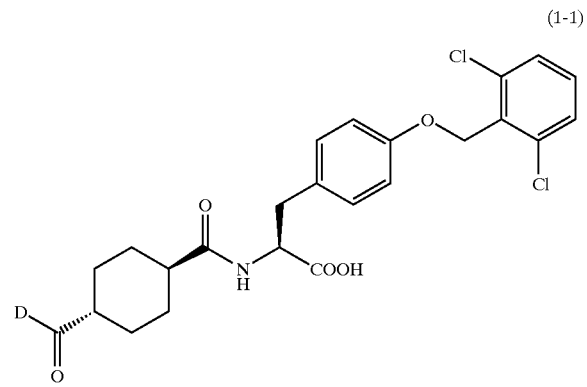

(1-1)

31 Claims, No Drawings

PHENYLALANINE DERIVATIVES

This application is a Continuation of prior International Application PCT/JP00/09223, filed Dec. 26, 2000.

BACKGROUND OF THE INVENTION

The present invention relates to new phenylalanine derivatives and the use of the phenylalanine derivatives as medicines. It was reported that a 4β7 integrin-depending adhesion process participates the pathology, such as inflammatory bowel diseases, diabetes, tumor proliferation and tumor metastasis. The compounds of the present invention having an antagonistic effect on the α4β7 integrins are usable as therapeutic agents or preventive agents for the above-described diseases.

It is generally understood that when a microorganism invades a living tissue or when the tissue is injured, inflammatory reactions play an important role for the exclusion of the microorganism or for the reparation of the injured tissue. As the technique of cytobiological analysis in inflammatory reactions developed, it has been elucidated that an excess progress of the inflammatory reactions plays an important role in causing various diseases including chronic diseases. Namely, by analyzing the inflammatory reactions in each disease, a method for controlling the inflammation in each disease is found and thus, it becomes possible to develop a new therapeutic method. For causing the inflammatory reactions, leukocytes usually circulating in the blood must pass through the vascular wall and be newly supplied to the injured tissue. The infiltration of the leukocytes from the blood vessel into the tissue is carried out by a series of different reactions subsequently occurred. Various cytokines released from the inflamed tissue activate the vascular-endothelium cells in the inflamed tissue and induce the expression of numerous cell surface antigens participating in the adhesion to leukocytes. They include, for example, E-selectin participating in the adhesion of neutrophils; ICAM-1 (Intercellular adhesion molecule-1) which participates in the interaction with LFA-1 (Leukocyte function-associated antigen-1) on the leukocytes; and VCAM-1 (Vascular cell adhesion molecule-1) which participates in the adhesion to α4β1 integrin (VLA-4 (Very late antigen-4)) on the leukocytes. When the leukocytes in the blood flow reach the activated vascular-endothelium, the leukocytes cause a phenomenon called "rolling" in which the leukocytes slowly roll on the vascular-endothelium cells. It was made evident that the rolling phenomenon occurs due to the interaction between selectin (particularly L-selectin) on the leukocytes and a particular sugar chain structure on the vascular-endothelium cells. It is generally said that for the extravascular infiltration of leukocytes, a strong adhesion by the interaction between integrin molecules which are a series of hetero-dimer protein on the leukocytes and the above-described cell-adhesion molecules on the vascular-endothelium such as ICAM-1 and VCAM-1 is necessitated after the weak interaction between the leukocytes and the vascular-endothelium cells due to the rolling phenomenon. Usually, integrin molecules expressing on the leukocytes have only a weak binding affinity for cell adhesion molecules expressing on the vascular-endothelium and, therefore, the adhesion is not strong. On the other hand, in an inflamed tissue, the leukocytes are activated by chemokine on the vascular-endothelium in the course of the rolling phenomenon of the leukocytes to reinforce the binding affinity with the integrin on the cell surfaces and thereby to make the strong adhesion and extravascular infiltration possible.

The leukocytes which infiltrate into an inflammatory site are mainly polymorphonuclear leukocytes in acute inflammations, but they are mainly lymphocytes or macrophages in chronic inflammations. Many kinds of lymphocytes do not return into a blood vessel after they once infiltrate into an extravascular tissue by an inflammatory stimulation. On the other hand, lymphocytes mainly comprising T cells and B cells participate in the control of immunologic reactions because they reciprocate between the extravascular tissue and the blood by so-called lymphocyte homing phenomenon in which they move from the blood into the lymphoid tissue through the vessel wall and then return into the blood through the lymph vessel even under physiological conditions. During the lymphocytes repeat the homing phenomenon, they meet an exogenous antigen in a peripheral tissue or a secondary lymphoid tissue and they are sensitized to the antigen. Thus, they differentiate from native cells into memory/effector cells. The lymphocytes thus differentiated into the memory/effector cells are divided into specified subsets and move into specified peripheral tissues such as the skin, lungs and mucosal tissue to control tissue-specific immunologic reactions and inflammatory reactions. Recently, a group of molecules having an important role for determining the tissue-specific homing reaction was elucidated. Namely, they are a homing receptor expressing on the lymphocytes and addressin expressing on the vascular-endothelium. It was elucidated that L-selectin on leukocytes and GlyCAM-1 (Glycosylation-dependent cell adhesion molecule-1) and CD34 on the vascular-endothelium act as the homing receptor and addressin, respectively, in the homing to the peripheral lymph node; that CLA (cutaneous lymphocyte antigen) and E-selectin similarly act in the homing to the skin; and that α4β7 integrin and MAdCAM-1 (mucosal addressin cell adhesion molecule-1) similarly act in the homing to the intestinal mucosa. In fact, Picker et al. proved that lymphocytes separated from the skin, pneumonic tissue and appendix highly express the respective homing receptors by using the actual tissues of patients (Picker et at., J. Immunol. 150:1122–1136, 1993 and Picker et al., Eur. J. Immunol. 24: 1269–1277, 1994). In the control of an inflammation reaction in a specified tissue, the inhibition of the adhesion mechanism concerning those tissue-specific homing is capable of realizing a more excellent selectivity toward the inhibition of the adhesion mechanism widely realized in the inflammation reaction. Thus, the above-described facts indicate the possibility of being the targets of an ideal medicine having only slight side reaction.

Inflammatory bowel diseases typified by ulcerative colitis and Crohn's disease are intractable inflammatory diseases because they gradually become chronic after the repetition of recurrence and remission. Although the cause of these diseases have not been elucidated, it is considered that an immunologic abnormality in the intestinal tissue strongly relates to the disease. It was also elucidated that an abnormality of the adhesion mechanism concerning the intestinal tissue-specific homing relates to these diseases. Briskin et al reported an increase in the expression of MAdCAM-1 in a location of intestinal inflammation in patients of inflammatory intestinal diseases such as Crohn's disease and ulcerative colitis (Briskin et al., Am. J. Pathol. 151: 97–110, 1997). Connor et al. recognized an increase in the expression of MAdCAM-1 i n a location of intestinal inflammation of each interleukin 10 knockout mouse which was one of the well recognized models of inflammatory bowel diseases (Connor et al., J. Leukoc. Biol. 65: 349–355, 1999). Further, in view of the fact that the conditions of mouse models suffering from inflammatory bowel diseases are improved by the administration of anti MAd CAM antibody or anti β7 integrin antibody in vivo, it is apparent that the acceleration of the adhesion mechanism of α4β7 integrin and MAdCAM-1 relates to the development of the diseases (Picarella et al., J. Immunol., 158: 2099–2106, 1997). Recently, it was elucidated that the acceleration of the mucosal tissue-specific homing mechanism concerns the development of insulin-dependent diabetes. Namely, Hanninen et al. reported that induction of the expression of MAdCAM-1 is observed in an inflamed tissue of Langerhans island of NOD mice which are models of an insulin-dependent diabetes (Hanninen et al., J. Immunol. 160: 6018–6025, 1998). Yang et al. reported that the disease of NOD mouse models is improved by the administration of anti β7 antibody (Yang et al., Diabetes 46: 1542–1547, 1997). It was also reported that in certain leukemia, the adhesion of β7 integrin to MAdCAM-1 is important for the metastatic infiltration into the mucosal tissues of digestive tracts (Chen et al., J. Clin. Immunol. 19: 186–193, 1999).

α4β7 integrin concerning the intestinal tissue-specific homing mechanism belongs to a 4 subfamily. As the integrins belonging to α4 subfamily, VLA-4 (very late antigen-4) molecules comprising α4β1 chain are known in addition to α4β7 integrin. The expression of VCAM-1 as the ligand of VLA-4 in the vascular-endothelium cells is induced systemically by substances causing the inflammation such as LPS (Lipopolysaccharide), TNF-α (Tumor necrosis factor-α) and IL-1. In the course of the inflammation, the infiltration of leukocytes from the blood flow into the inflammatory tissue is conducted by the VLA-4/VCAM-1 adhesion mechanism (Elices, Cell 60: 577–584, 1990, Osborn et al., Cell 59:1203–1211, 1989, Issekutz et al., J. Eex. Med. 183: 2175–2184, 1996). The participation of the adhesion mechanism of α4β1/VCAM-1 in various pathological stages was reported with reference to the patients with autoimmune diseases such as rheumatoid synovial membrane (van Dinther-Janssen, J. Immunol. 147: 4207–4210, 1991 and Morales-Ducret et al., J. Immunol. 149: 1424–1431, 1992), lungs and respiratory tract epithelium in asthma (ten Hacken et al., Clin. Exp. Allergy 12: 1518–1525, 1998) and allergic diseases (Randolph et al., J. Clin. Invest. 104: 1021–1029, 1999), systemic erythematodes (Takeuchi et al., J. Clin. Invest. 92: 3008–3016, 1993), Sjogren's syndrome (Edwards et al., Ann. Rheum. Dis. 52: 806–811, 1993), multiple sclerosis (Steffen et al., Am. J. Pathol. 145: 189–201, 1994) and psoriasis (Groves et al., J. Am. Acad. Dermatol. 29: 67–72, 1993). Also in the infiltration of virus-disturbing CD8 positive T cells into a virus-sensitized location, the α4β1/VCAM adhesion mechanism is employed (Christensen et al., J. Immunol. 154: 5293–5301, 1995). The above-described facts prove that the α4β1/VCAM-1 adhesion mechanism participates in not only the inflammation stage in the mucosal tissue but also the systemic, general inflammation reactions.

Further, it was elucidated that the binding specificity of α4β1 integrin is similar to that of α4β7 integrin because of the similarity in the structure of them. Only α4β7 integrin has the binding specificity to the above-described MAdCAM-1. On the other hand, VCAM-1 and fibronectin which are other ligands known to be capable of binding to α4β7 integrin are also capable of binding to α4β1 integrin. Many of integrins using extracellular matrixes as the ligands, such as VLA-5β-3 subfamily and β-5 subfamily, recognize arginine-glycine-aspartic acid (RGD) sequence in fibronectin, vitronectin, tenascin and osteopontin. On the other hand, in the interaction of α4β1 and α4β7 with fibronectin, the RGD sequence does not participate but a CS1 peptide part comprising leucinie-aspartic acid-valine (LDV) as the core sequence participates. Clements et al. found a sequence similar to LDV in amino acid sequences of VCAM-1 and MAdCAM-1. It was elucidated that a variant obtained by partially modifying the CS-1-like sequence of VCAM-1 and MAdCAM-1 molecules cannot interact with α4β1 integrin and α4β7 integrin (Clements et al., Vonderheide et al., Renz et al.). Thus, it was found that the CS-1-like sequence is important for the interaction of α4β1/α4β7 with VCAM-1/MAdCAM-1. It was reported that the same cyclic peptide having the CS-1-like structure is antagonistic to the interaction of α4β1 and α4β7 with VCAM-1, MAdCAM-1 or CS-1 peptide (Vanderslice et al., JI 158: 1710, 1997). The above-described facts indicate that the selective control of the binding specificity of α4β7 and α4β1 is difficult.

As described above, the adhesion mechanism of α4β7 and VCAM-1 widely concerns the inflammation reaction in the whole body including the inflammation process in mucosal tissues. A suitable α4 integrin antagonist capable of inhibiting the adhesion of both α4β1 and α4β7 is usable as a therapeutic agent for these ordinary inflammatory diseases. However, taking the control of chronic inflammations in intestinal mucosal tissue in a case of, for example, an inflammatory bowel disease into consideration, it is undesirable to inhibit the adhesion of both α4β1 and α4β7 for a long time because a risk of the systemic infection or the like is increased, while the inflammation reaction in the intestinal tissue can be inhibited. Also from the viewpoint of the safety, it is desirable to control only the α4β7 adhesion pathway which is more specific to the inflammation of intestinal mucosa.

Thus, the finding of a suitable antagonist which is inert to α4β1 but specifically reactive on α4β7 makes it possible to use the antagonist as a therapeutic agent for the above-described inflammatory bowel diseases and diabetes and also for controlling metastasis of some kinds of leukemia. The use of peptide compounds and amino acid derivatives as the antagonists to α4 integrin is described in WO 94/15958, WO 95/15973, WO 96/00581, WO 96/06108, WO 99/10313, WO 99/36393, etc. However, those antagonists have only an insufficient selectivity toward α4β7 and they are unsuitable for use as antagonists specific to α4β7. Thus, there is no antagonist specific to α4β7 and practically usable for the therapeutic purpose at present.

DISCLOSURE OF THE INVENTION

An object of the present invention is to provide new compounds antagonistic to α4β7 integrin.

Another object of the present invention is to provide an antagonist to α4β7 integrin.

A still another object of the present invention is to provide a therapeutic agent or preventive agent for diseases in which α4β7 integrin-depending adhesion process participates in the pathology, such as inflammatory bowel diseases, diabetes, tumor proliferation and tumor metastasis.

A further object of the present invention is to provide a pharmaceutical composition containing such a new compound.

After synthesizing various phenylalanine derivatives and examining α4 integrin antagonistic activities thereof for the purpose of solving the above-described problems, the inventors have found that specified, new phenylalanine derivatives, particularly compounds of the following general formula (1), have excellent antagonistic activity to α4β7 integrin and selectivity to other integrins such as α4β1 integrin. The present invention has been completed on the basis of this finding.

Namely, the present invention provides phenylalanine derivatives of the following general formula (1) and pharmaceutically acceptable salts thereof:

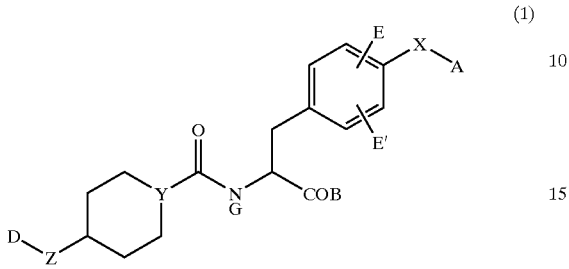

(1)

wherein X represents an interatomic bond, —O—, —O—SO$_2$—, —NR$^1$—, —NR$^1$—C(=O)—, —NR$^1$—SO$_2$—, —NR$^1$—C(=O)—NH—, —NR$^1$—C(=S)—NH— or —C(=O)—, wherein R$^1$ represents a hydrogen atom, a lower alkyl group, a lower alkenyl group, a lower alkenyl group, a lower alkyl group substituted with a cycloalkyl group which may contain a hetero atom(s) in the ring thereof, a lower alkyl group substituted with an aryl group or a lower alkyl group substituted with a heteroaryl group;

Y represents N or CH;

Z represents —C(=O)—, —S(=O)— or —SO$_2$—;

A represents a group of the following general formula (2), a lower alkyl group, a lower alkenyl group, a lower alkynyl group, a cycloalkyl group which may contain a hetero atom(s) in the ring thereof, an aryl group, a heteroaryl group, a lower alkyl group substituted with a cycloalkyl group which may contain a hetero atom(s) in the ring thereof, a lower alkyl group substituted with a group of general formula (2), a lower alkyl group substituted with an aryl group, a lower alkyl group substituted with a heteroaryl group, a lower alkenyl group substituted with a cycloalkyl group which may contain a hetero atom(s) in the ring thereof, a lower alkenyl group substituted with an aryl group, a lower alkenyl group substituted with a heteroaryl group, a lower alkynyl group substituted with a cycloalkyl group which may contain a hetero atom(s) in the ring thereof, a lower alkynyl group substituted with an aryl group or a lower alkynyl group substituted with a heteroaryl group:

(2)

wherein R$^2$, R$^3$, R$^4$, R$^5$ and R$^6$ may be the same or different from one another, and each represents a hydrogen atom, a halogen atom, a hydroxyl group, a lower alkyl group, a lower alkenyl group, a lower alkynyl group, a cycloalkyl group which may contain a hetero atom(s) in the ring thereof, an aryl group, a heteroaryl group, a lower alkyl group substituted with a cycloalkyl group which may contain a hetero atom(s) in the ring thereof, a lower alkyl group substituted with an aryl group, a lower alkyl group substituted with a heteroaryl group, a lower alkoxyl group, a lower alkoxyl group substituted with a cycloalkyl group which may contain a hetero atom(s) in the ring thereof, a lower alkoxyl group substituted with an aryl group, a lower alkoxyl group substituted with a heteroaryl group, a cycloalkyloxy group which may contain a hetero atom(s) in the ring thereof, an aryloxy group, a heteroaryloxy group, a hydroxy-lower alkyl group, a hydroxy-lower alkenyl group, a hydroxy-lower alkoxyl group, a halogeno-lower alkyl group, a halogeno-lower alkenyl group, a halogeno-lower alkoxyl group, a halogeno-lower alkenyl group, a nitro group, a cyano group, a substituted or unsubstituted amino group, a carboxyl group, a lower alkyloxycarbonyl group, a substituted or unsubstituted carbamoyl group, a lower alkanoyl group, an aroyl group, a lower alkylthio group, a lower alkylsulfonyl group or a substituted or unsubstituted sulfamoyl group;

B represents a hydroxyl group, a lower alkoxyl group or a hydroxyamino group;

G represents hydrogen atom, a lower alkyl group, a lower alkenyl group, a lower alkynyl group, a lower alkyl group substituted with a cycloalkyl group which may contain a hetero atom(s) in the ring thereof, a lower alkyl group substituted with an aryl group or a lower alkyl group substituted with a heteroaryl group;

D represents OR$^7$, NR$^7$R$^8$, NHNR$^7$R$^8$, NR$^7$NHR$^8$, SR$^7$ or R$^7$, wherein R$^7$ and R$^8$ may be the same or different from each other and each represents a hydrogen atom, a lower alkyl group, a lower alkenyl group, a lower alkynyl group, a cycloalkyl group which may contain a hetero atom(s) in the ring thereof, an aryl group, a heteroaryl group, a lower alkyl group substituted with a cycloalkyl group which may contain a hetero atom(s) in the ring thereof, a lower alkyl group substituted with an aryl group, a lower alkyl group substituted with a heteroaryl group, a lower alkenyl group substituted with a cycloalkyl group which may contain a hetero atom(s) in the ring thereof, a lower alkenyl group substituted with an aryl group, a lower alkenyl group substituted with a heteroaryl group, a lower alkynyl group substituted with a cycloalkyl group which may contain a hetero atom(s) in the ring thereof, a lower alkynyl group substituted with an aryl group, a lower alkynyl group substituted with a heteroaryl group, a halogeno-lower alkyl group, a halogeno-lower alkenyl group, a hydroxy-lower alkyl group, a hydroxy-lower alkenyl group or a substituted or unsubstituted amino-lower alkyl group, or R$^7$ and R$^8$ may be bonded together to form a ring which may contain one or two oxygen, nitrogen or sulfur atoms; and the substituent of the ring is a hydrogen atom, a halogen atom, hydroxyl group, a lower alkyl group, a lower alkenyl group, a lower alkynyl group, a cycloalkyl group which may contain a hetero atom(s) in the ring thereof, an aryl group, a heteroaryl group, a lower alkyl group substituted with a cycloalkyl group which may contain a hetero atom(s) in the ring thereof, a lower alkyl group substituted with an aryl group, a lower alkyl group substituted with a heteroaryl group, a lower alkanoyl group, an aroyl group, a halogeno-lower alkanoyl group, a lower alkyloxy group, nitro group, cyano group, a substituted or unsubstituted amino group, carboxyl group, a lower alkoxycarbonyl group, a substituted or unsubstituted carbamoyl group, a lower alkylthio group, a lower alkylsulfonyl group or a substituted or unsubstituted sulfamoyl group; and E and E' may be the same or different from each other and each represents a hydrogen atom, a halogen atom, a lower alkyl group, a lower alkyloxy group or nitro group.

The present invention provides an α4β7 integrin antagonist containing the above-described phenylalanine derivative or a pharmaceutically acceptable salt thereof as the active ingredient.

The present invention also provides a therapeutic agent or preventive agent and a pharmaceutical composition containing the phenylalanine derivative or a pharmaceutically acceptable salt thereof as the active ingredient, for diseases in which α4β7 integrin-depending adhesion process participates in the pathology, such as inflammatory intestinal diseases, diabetes, tumor proliferation and tumor metastasis.

BEST MODE FOR CARRYING OUT THE INVENTION

The term "lower" in, for example, a lower alkyl group indicates that the group has 1 to 6 carbon atoms. Alkyl groups per se and also alkyl groups in alkenyl groups, alkynyl groups, alkoxyl groups, alkylthio groups, alkanoyl groups and alkylamino groups, alkenyl groups and alkynyl groups may be either linear or branched. Examples of these alkyl groups include methyl group, ethyl group, propyl group, isopropyl group, butyl group, secondary butyl group, tertiary butyl group, pentyl group and hexyl group. The alkenyl groups are, for example, vinyl group, propenyl group, butenyl group and pentenyl group. The alkynyl groups include ethynyl group, propynyl group, butynyl group, etc. The cycloalkyl groups include cyclopropyl group, cyclobutyl group, cyclopentyl group, cyclohexyl group, norbornyl group, adamantyl group, cyclohexenyl group, etc. The alkoxyl groups include methoxyl group, ethoxyl group, propyloxy group, isopropyloxy group, etc. The hetero atoms include nitrogen atom, oxygen atom, sulfur atom, etc. The halogen atoms are fluorine atom, chlorine atom, bromine atom and iodine atom. The halogenoalkyl groups include chloromethyl group, trichloromethyl group, trifluoromethyl group, trifluoroethyl group, pentafluoroethyl group, etc. The halogenoalkoxyl groups include trichloromethoxyl group, trifluoromethoxyl group, etc. The hydroxyalkyl groups include hydroxymethyl group, hydroxyethyl group, etc. The cycloalkyl groups which may contain a hetero atom(s) in the ring thereof include piperidyl group, piperazinyl group, morpholinyl group, pyrrolidinyl group, tetrahydrofuranyl group, etc. They also include piperidino group and morpholino group.

In the present specification, the aryl groups are both substituted and unsubstituted aryl groups such as phenyl group, 1-naphthyl group and 2-naphthyl group. They are preferably phenyl group and substituted phenyl group, and the substituents are particularly preferably halogen atoms, alkoxyl groups, alkyl groups, hydroxyl group, halogenoalkyl groups and halogenoalkoxyl groups. The heteroaryl groups are both substituted and unsubstituted heteroaryl groups such as pyridyl group, pyrimidinyl group, furyl group, thienyl group, indolyl group, quinolyl group, isoquinolyl group and 1,2,3-thiadiazolyl group. Preferred heteroaryl groups are pyridyl group, pyrimidinyl group, furyl group, thienyl group and 1,2,3-thiadiazolyl group and substituted pyridyl, pyrimidinyl, furyl, thienyl and 1,2,3-thiadiazolyl groups. Particularly preferred substituents are halogen atoms, alkoxyl groups, alkyl groups, hydroxyl group, halogenoalkyl groups and halogenoalkoxyl groups. The lower alkyl groups substituted with an aryl group include, for example, benzyl group and substituted benzyl groups. Particularly preferred substituents are halogen atoms, alkoxyl groups, alkyl groups, hydroxyl group, halogenoalkyl groups and halogenoalkoxyl groups. The lower alkyl groups substituted with a heteroaryl group include, for example, pyridylmethyl group, and particularly preferred substituents thereof are halogen atoms, alkoxyl groups, alkyl groups, hydroxyl group, halogenoalkyl groups and halogenoalkoxyl groups. The alkanoyl groups include, for example, formyl groups, acetyl groups, propanoyl group, butanoyl group and pivaloyl group. The aroyl groups include, for example, substituted or unsubstituted benzoyl group and pyridylcarbonyl group, and the substituents thereof are particularly preferably halogen atoms, alkoxyl groups, alkyl groups, hydroxyl group, halogenoalkyl groups and halogenoalkoxyl groups. The halogenoalkanoyl groups include, for example, trichloroacetyl group and trifluoroacetyl group. The alkylsulfonyl groups include, for example, methanesulfonyl group, ethanesulfonyl group, etc. The arylsulfonyl groups include, for example, benzenesulfonyl group and p-toluenesulfonyl group. The heteroarylsulfonyl groups include, for example, pyridylsulfonyl group. The halogenoalkylsulfonyl groups include, for example, trifluoromethanesulfonyl group. The alkyloxycarbonyl groups include, for example, methoxycarbonyl group, ethoxycarbonyl group and tertiary butoxycarbonyl group. The aryl-substituted alkoxycarbonyl groups include, for example, benzyloxycarbonyl group and 9-fluorenylmethoxycarbonyl group. The substituted carbamoyl groups include, for example, methylcarbamoyl group, phenylcarbamoyl group and substituted phenylcarbamoyl group, and the substituents thereof are particularly preferably halogen atoms, alkoxyl groups, alkyl groups, hydroxyl group, halogenoalkyl groups and halogenoalkoxyl groups. The substituted thiocarbamoyl groups include, for example, methylthiocarbamoyl group, phenylthiocarbamoyl group and substituted phenylthiocarbamoyl groups, and the substituents thereof are particularly preferably halogens, alkoxyl groups, alkyl groups, hydroxyl group, halogenoalkyl groups and halogenoalkoxyl groups. The substituents in the substituted amino groups herein include lower alkyl groups, lower alkyl groups substituted with an aryl group, lower alkyl groups substituted with a heteroaryl group, lower alkanoyl groups, aroyl groups, halogeno-lower alkanoyl groups, lower alkylsulfonyl groups, arylsulfonyl groups, heteroarylsulfonyl groups, halogenoalkylsulfonyl groups, lower alkyloxycarbonyl groups, aryl-substituted lower alkyloxycarbonyl groups, substituted or unsubstituted carbamoyl groups and substituted or unsubstituted thiocarbamoyl groups.

The group represented by X in the above general formula (1) is preferably an interatomic bond, —O—, —O—SO$_2$—, —NR$^1$—, —NR$^1$—C(=O)— or —NR$^1$—SO$_2$—. The group represented by X is particularly preferably —O—, —NR$^1$—C(=O)— or an interatomic bond.

The group represented by Y is preferably CH.

The group represented by Z is preferably —C(=O)— or —SO$_2$—.

In the groups represented by A, the cycloalkyl groups which may contain a hetero atom(s) in the ring thereof, aryl groups and heteroaryl groups are either substituted or unsubstituted. The substituents thereof are those described above with reference to R$^2$ to R$^6$. The groups represented by A are preferably lower alkyl groups substituted with a group of general formula (2), groups of general formula (2) and heteroaryl groups.

The group represented by B is preferably a hydroxyl group or a lower alkoxyl group. It is particularly preferably a hydroxyl group.

The group represented by C is preferably a hydrogen atom.

In the groups represented by $R^7$ or $R^8$ among those represented by D, the cycloalkyl groups which may contain a hetero atom(s) in the ring thereof, aryl groups and heteroaryl groups are either substituted or unsubstituted, and the substituents are those described above with reference to $R^2$ to $R^6$. Examples of the groups, formed when D represents a group of the formula: $NR^7R^8$ wherein $R^7$ and $R^8$ together form a ring structure, include 1-piperidyl group, piperazine-1-yl group, morpholine-4-yl group and pyrrolidine-1-yl group.

As the groups represented by D, those represented by $OR^7$, $NR^7R^8$, $NHNR^7R^8$, $NR^7NHR^8$ or $SR^7$ are preferred. $NR^7R^8$, $NHNR^7R^8$, $NR^7NHR^8$ or $SR^7$ is more preferred. $NR^7R^8$ or $NHNR^7R^8$ is particularly preferred. $R^7$ and $R^8$, which may be the same or different from each other, are each preferably a hydrogen atom, a lower alkyl group, a cycloalkyl group which may contain a hetero atom(s) in the ring thereof, an aryl group, a heteroaryl group, a lower alkyl group substituted with a cycloalkyl group which may contain a hetero atom(s) in the ring thereof, a lower alkyl group substituted with an aryl group, or a lower alkyl group substituted with a heteroaryl group. It is also preferred that $R^7$ and $R^8$ are bonded to each other to form a ring which may contain 1 or 2 oxygen atoms, nitrogen atoms or sulfur atoms. The substituents of the ring are preferably a hydrogen atom, halogen atoms, hydroxyl group, lower alkyl groups, aryl groups, heteroaryl groups, lower alkyl groups substituted with an aryl group, lower alkanoyl groups, aroyl groups, lower alkyloxy groups, nitro group, cyano groups, substituted or unsubstituted amino groups, carboxyl group, lower alkoxycarbonyl groups, lower alkoxycarbonyl groups substituted with an aryl group, substituted or unsubstituted carbamoyl group, substituted or unsubstituted thiocarbamoyl group, lower alkylthio groups, lower alkylsulfonyl groups and substituted or unsubstituted sulfamoyl group. The groups represented by D are preferably hydroxyl group, phenylhydrazino group, 4-bromophenylhydrazino group, 4-rethoxyphenylhydrazino group, 4-cyanophenylhydrazino group, 4-methylphenylhydrazino group, 4-trifluoromethoxyhydrazino group, 3-methoxyphenylhydrazino group, etc.

The group represented by E or E' is preferably a hydrogen atom.

The groups represented by $R^2$ to $R^6$ are more preferably a hydrogen atom, halogen atoms, hydroxyl group, lower alkyl groups, lower alkoxyl groups, halogeno-lower alkyl groups and halogeno-lower alkoxyl groups.

It is preferred that in general formula (1) in the present invention, X represents an interatomic bond or a group of the formula: —O—, —O—SO$_2$—, —NR$^1$—, —NR$^1$—C(=O)— or —NR$^1$—SO$_2$—, Y represents a group of the formula: —CH, Z represents a group of the formula: —C(=O)—, A represents a group of general formula (2), a lower alkyl group, a lower alkenyl group, a lower alkynyl group, a cycloalkyl group which may contain a hetero atom(s) in the ring thereof, an aryl group, a heteroaryl group, a lower alkyl group substituted with a cycloalkyl group which may contain a hetero atom(s) in the ring thereof, a lower alkyl group substituted with a group of general formula (2), a lower alkyl group substituted with an aryl group or a lower alkyl group substituted with a heteroaryl group, B represents a hydroxyl group or a lower alkoxyl group, and C represents a hydrogen atom or a lower alkyl group.

It is preferred that (i) in general formula (1), X represents a group of the formula: —O—, Y represents a group of the formula: CH, Z represents a group of the formula: —C(=O)—, A represents a lower alkyl group substituted with a group of general formula (2), $R^2$, $R^3$, $R^4$, $R^5$ and $R^6$ may be the same or different from one another, and each represents a hydrogen atom or a halogen atom, B represents hydroxyl group or a lower alkoxyl group, C represents a hydrogen atom, D represents $OR^7$, $NR^7R^8$ or $NHNR^7R^8$, $R^7$ and $R^8$ may be the same or different from each other and each represents a hydrogen atom, a lower alkyl group, a cycloalkyl group which may contain a hetero atom(s) in the ring thereof, an aryl group, a heteroaryl group, a lower alkyl group substituted with a cycloalkyl group which may contain a hetero atom(s) in the ring thereof, a lower alkyl group substituted with an aryl group or a lower alkyl group substituted with a heteroaryl group, or $R^7$ and $R^8$ may be bonded together to form a ring which may contain one or two oxygen, nitrogen or sulfur atoms; and the substituents of the ring include a hydrogen atom, a halogen atom, hydroxyl group, a lower alkyl group, a lower alkenyl group, a lower alkynyl group, a cycloalkyl group which may contain a hetero atom(s) in the ring thereof, an aryl group, a heteroaryl group, a lower alkyl group substituted with a cycloalkyl group which may contain a hetero atom(s) in the ring thereof, a lower alkyl group substituted with an aryl group, a lower alkyl group substituted with a heteroaryl group, a lower alkanoyl group, an aroyl group, a halogeno-lower alkanoyl group, a lower alkyloxy group, nitro group, cyano group, a substituted or unsubstituted amino group, carboxyl group, a lower alkyloxycarbonyl group, a substituted or unsubstituted carbamoyl group, a lower alkylthio group, a lower alkylsulfonyl group or a substituted or unsubstituted sulfamoyl group, and E and E' each represents a hydrogen atom.

It is preferred that in above condition (i), X represents a group of the formula: —NR$^1$—C(=O)—, Y represents a group of the formula: CH, Z represents a group of the formula: —C(=O)— and A represents a heteroaryl group. It is also preferred that X represents an interatomic bond, Y represents a group of the formula: CH, Z represents a group of the formula: —C(=O)— and A represents a group of general formula (2).

The following compounds and pharmaceutically acceptable salts thereof are preferred:

N-(trans-4-carboxycyclohexane-1-carbonyl)-O-(2,6-dichlorobenzyl)-L-tyrosine;

N-(trans-4-phenylhydrazinocarbonylcyclohexane-1-carbonyl)-O-(2,6-dichlorobenzyl)-L-tyrosine; and N-[trans-4-(4-bromophenylhydrazinocarbonyl)cyclohexane-1-carbonyl]-O-(2,6-dichlorobenzyl)-L-tyrosine.

The following compounds and pharmaceutically acceptable salts thereof are preferred:

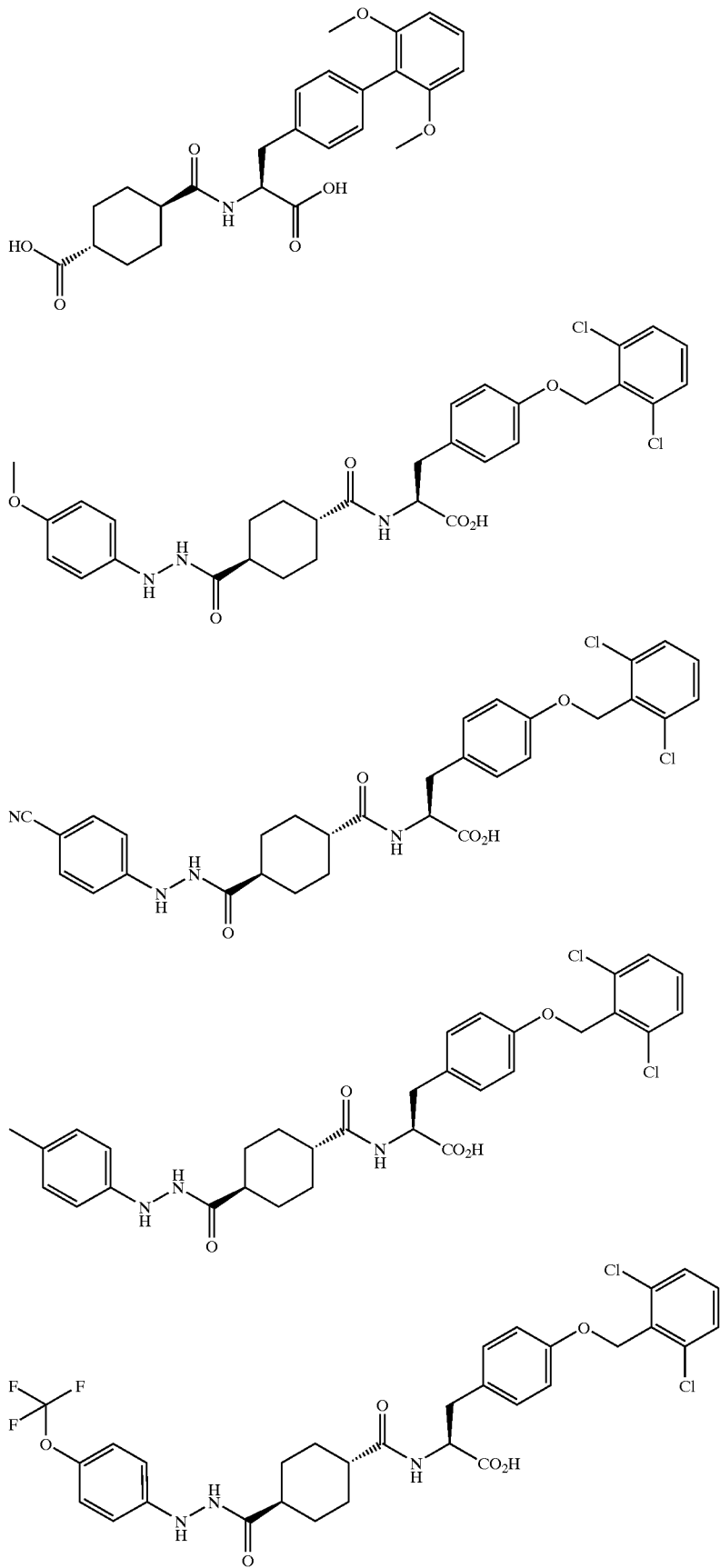

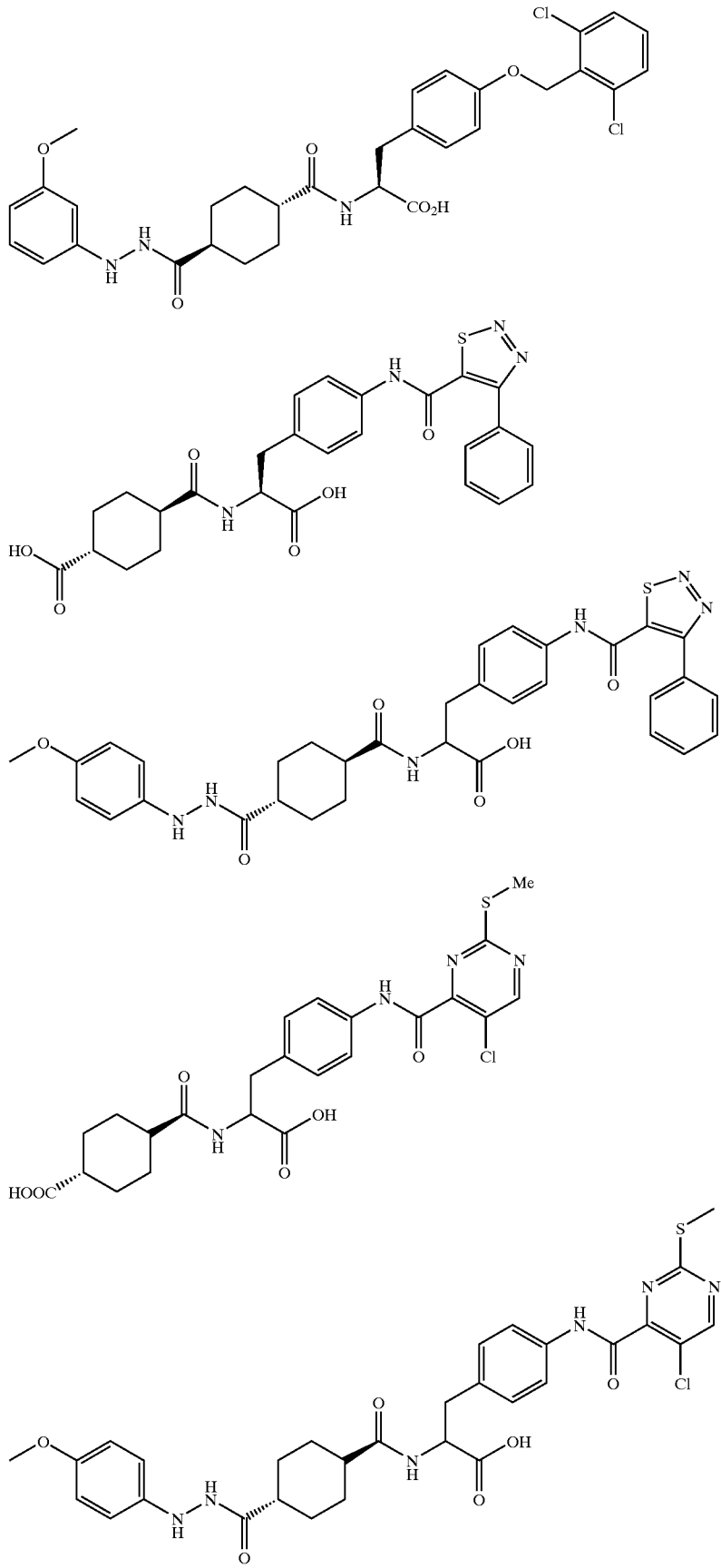

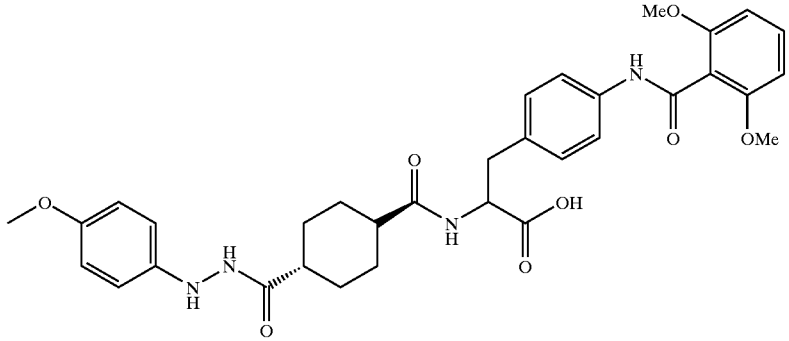

The phenylalanine derivatives (1) of the present invention can be synthesized by methods described below. For example, a phenylalanine derivative (8) of general formula (1) wherein —X—A represents a group defined by Q described below, Y represents a group of the formula: CH, Z represents a group of the formula: —C(=O)—, B represents hydroxyl group and C represents a hydrogen atom can be synthesized as shown below. A symbol "●" in schemes 5 and 6 represents a resin such as Wang resin.

Scheme 5

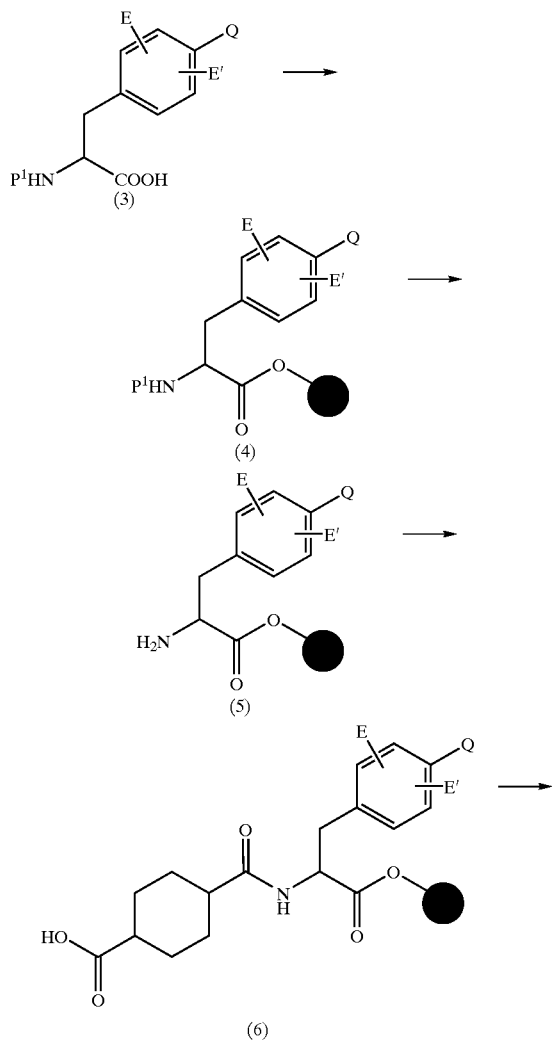

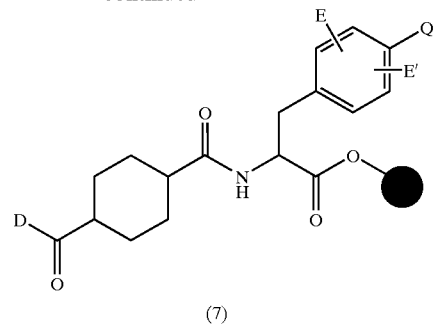

A suitably protected carboxylic acid (3) is attached to a resin by a usual method. The substituent Q of the carboxylic acid (3) has a structure of —X—A as described above with reference to the general formula (1), it is a substituent convertible into —X—A in any stage of the synthesis or it has a suitably protected structure. As for the attachment reaction conditions, the reaction can be conducted by using, if necessary, a suitable additive such as HOAt (1-hydroxy-7-azabenzotriazole) or HOBt (1-hydroxybenzotriazole) and a condensing agent such as DIC (diisopropylcarbodiimide), DCC (dicyclohexylcarbodiimide) or EDC (1-ethyl-3-(3-dimethylaminopropyl)carbodiimide) in an organic solvent such as dichloromethane, DMF (N,N-dimethylformamide) or NMP (N-methyl-2-pyrrolidone). For example, when Wang resin is used, the reaction is carried out in the presence of pyridine and 2,6-dichlorobenzoyl chloride in DMF to obtain an ester (4). A protective group $P^1$ is removed from the ester (4) under suitable conditions to obtain an amine (5). For example, when Fmoc group (9-fluorenylmethoxycarbonyl group) is used as $P^1$, the protective group can be removed with a base such as piperidine in a solvent such as DMF. The amine (5) can be converted into a carboxylic acid (6) by condensing it with 1,4-cyclohexanedicarboxylic acid (11) by using a condensing agent such as DIC and, if necessary, a suitable additive such as HOAt or HOBt in an organic solvent such as DMF, NMP or dichloromethane. The carboxylic acid (6) can be converted into a carbonyl derivative (7) by reacting it with an amine, an alcohol, a hydrazine or a thiol under the same conditions as those in the above-described condensation reaction.

Scheme 6

(5) →(12)

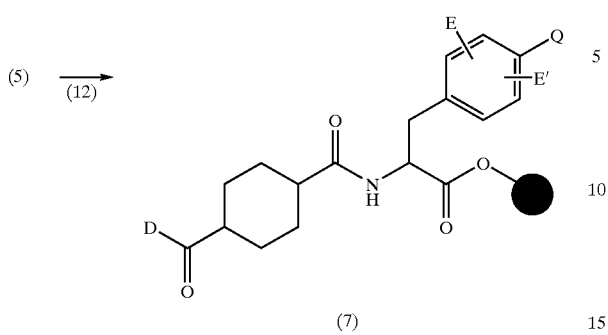

(7)

The amine (5) can be converted into a carbonyl derivative (7) by reacting it with a carboxylic acid (12), synthesized by a method described later, under the above-described condensation reaction conditions.

Scheme 7

(7) →

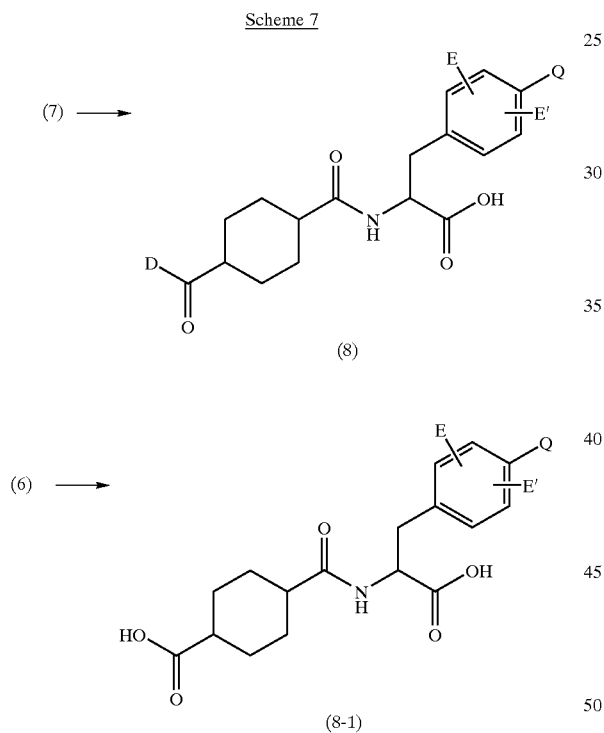

(8)

(6) →

(8-1)

The carbonyl derivative (7) obtained as described above is cleaved from the resin under suitable conditions to obtain it in the form of a carboxylic acid (8). For example, when Wang resin is used as the resin, the product is treated with an acid reaction solution containing, for example, TFA (trifluoroacetic acid) to obtain a carboxylic acid (8) solution and then the solvent is evaporated to obtain a carboxylic acid (8). The carboxylic acid (8) thus obtained is purified by the column chromatography, HPLC, recrystallization or the like to obtain the pure carboxylic acid (8).

The compounds of the general formula (1) can be synthesized also by the following method:

Scheme 8

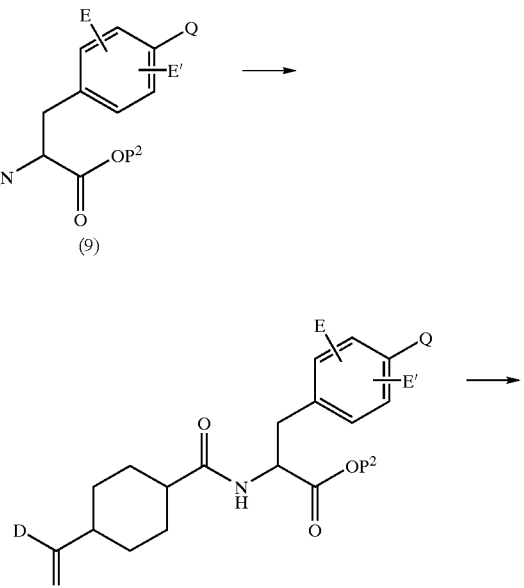

(9)

(10)

(8)

A suitably protected amine (9) is reacted with 1,4-cyclohexanedicarboxylic acid or a carboxylic acid (12), synthesized by a method described later, by using, if necessary, a suitable additive such as HOAt or HOBt and a condensing agent such as DIC, DCC or EDC in an organic solvent such as dichloromethane, DMF or NMP to obtain a carbonyl derivative (10). The substituent Q of the amine (9) has a structure of —X—A as described above with reference to the general formula (1), or it is a substituent convertible into —X—A in any stage of the synthesis, or the substituent is suitably protected. The protective group is removed from thus obtained carbonyl derivative (10) under suitable reaction conditions to obtain the carboxylic acid (8). For example, the protective group can be removed by the alkali hydrolysis when $P^2$ is methyl or ethyl group, or by the treatment with an acidic solution when $P^2$ is t-butyl group or by the hydrolysis or by the reaction with hydrogen in the presence of a metal catalyst when $P^2$ is benzyl group or the like. When 1,4-cyclohexanedicarboxylic acid (11) is used as the starting carboxylic acid, a carboxylic acid (8) is obtained via a carbonyl derivative (10) of the above formula wherein D represents hydroxyl group.

The carboxylic acid (12) can be synthesized by the following method:

Scheme 9

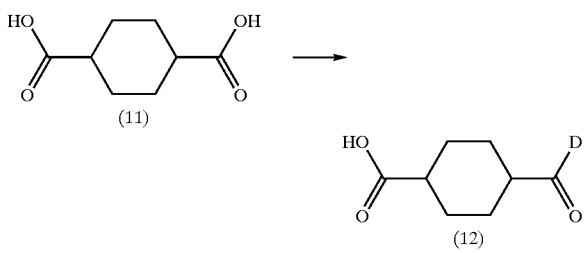

Namely, 1,4-cyclohexanedicarboxylic acid (11) is reacted with a suitable amount of an amine, an alcohol, a hydrazine or a thiol by using a suitable condensing agent such as DIC, DCC or EDC in the presence of a suitable additive in a suitable organic solvent such as dichloromethane or DMF and then the product is purified by a suitable method such as column chromatography or recrystallization to obtain the carboxylic acid (12).

Scheme 10

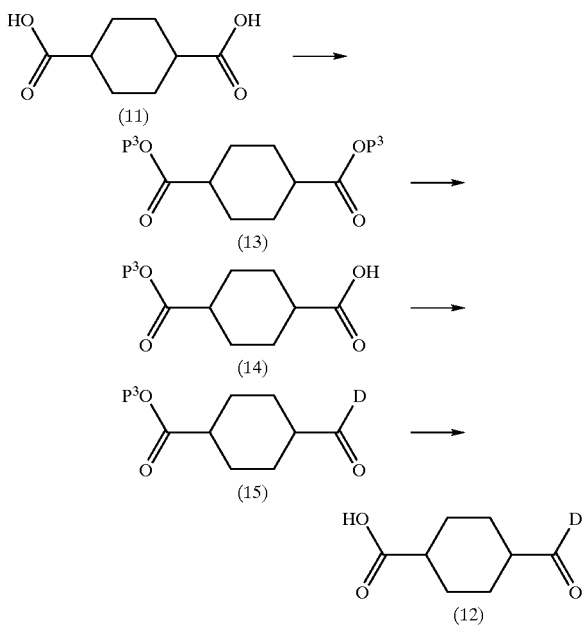

A monocarboxylic acid (14) can be obtained by esterifying 1,4-cyclohexanedicarboxylic acid (11) by an ordinary method to form a diester (13) and then reacting the diester (13) with a suitable amount of a base such as sodium hydroxide, potassium hydroxide or lithium hydroxide in an organic solvent such as methanol, ethanol or THF or in a mixture of the organic solvent with water. The inonocarboxylic acid (14) is reacted with a suitable amount of an amine, an alcohol, a hydrazine or a thiol by using a suitable condensing agent such as DIC, DCC or EDC in the presence of a suitable additive in a suitable solvent such as dichloromethane or DMF to obtain a carbonyl derivative (15) and then this product is hydrolyzed under the same reaction conditions as those described above to obtain the carboxylic acid (12).

Various partial structures represented by —X—A in the general formula (1) can be synthesized from corresponding precursors by reactions described below. By the reactions described below, Q in the precursor structure can be converted into —X—A in a suitable stage in the steps in schemes 5 to 8 which are ordinary methods for synthesizing the compounds of the general formula (1).

When Q is hydroxyl group or a suitably protected hydroxyl group, the protective group is removed, if necessary, to form hydroxyl group and then the subsequent conversion reaction can be conducted as described below.

Hydroxyl group Q can be reacted with an alkylating agent such as an alkyl halide or an alkyl sulfonate in the presence of a suitable base in an organic solvent to form various ether-type structures. The ether-type compounds can be formed also by subjecting the obtained compound to Mitsunobu reaction with an alcohol in the presence of a dialkylazodicarboxylic acid. The compounds having structures of various aryl ether types or heteroaryl ether types can be formed by reacting the obtained compound with an aryl halide or a heteroaryl halide in the presence of a suitable base or catalyst in an organic solvent.

Hydroxyl group Q can be reacted with a sulfonic acid halide or sulfonic acid anhydride in the presence of an organic base such as triethylamine, diIsopropylethylamine, pyridine or N,N-dimethylaminopyridine or an inorganic base such as potassium carbonate or sodium carbonate in an organic solvent such as DMF or dichloromethane to form a corresponding product having a sulfonic acid ester type structure.

A trifluoromethanesulfonic acid ester (hereinafter referred to as "triflate" can be obtained under the above-described sulfonation reaction conditions. The triflate can be converted into an aryl-substituted compound or a heteroaryl-substituted compound by Suzuki coupling reaction wherein it is reacted with a boric acid compound in the presence of a palladium catalyst such as tetrakistriphenylphosphine palladium or palladium acetate or another metal catalyst in a solvent such as DMF, DME (1,2-dimethoxyethane), toluene or dioxane at room temperature or under heating. The conversion reaction into the aryl-substituted compounds can be carried out by using not only the triflate but also a compound of the above formula wherein Q is substituted with a halogen atom.

When Q is a properly protected amino group, the protective group can be removed to form the amino group by a method suitably selected depending on the protective group. When Q is nitro group, it can be converted into the amino group by the hydrogenation reaction in the presence of a metal catalyst or by the reduction reaction with a reducing agent selected from the group consisting of various reducing agents. The amino group thus obtained can be further converted into groups of various structures by various reactions described below.

The amino group can be further converted into an alkylamino group by reacting it with an alkylating agent such as an alkyl halide or an alkyl sulfonate in the presence of a suitable base in an organic solvent. Various arylamine structures can be formed by reacting the amino group with an aryl halide in the presence of a suitable base in an organic solvent.

The amino group can be converted into an alkylamino group by reacting it with an aldehyde or a ketone in the presence of a reducing agent such as sodium borohydride or sodium cyanoborohydride in a solvent such as DMF, dichloromethane, a trialkylorthoformic acid or a trialkylorthoacetic acid. The amino group or alkylamino group can be converted into groups of various structures by reactions described below.

The amino group or alkylamino group can be converted into a corresponding structure of amide type or sulfonamide type by reacting it with a carboxylic acid halide, a carboxylic acid anhydride, a sulfonic acid halide or a sulfonic acid anhydride in the presence of an organic base such as triethylamine, diisopropylethylamine, pyridine or N,N-dimethylaminopyridine or an inorganic base such as potassium carbonate or sodium carbonate in an organic solvent such as DMF or dichloromethane. The amino group or alkylamino group can be converted into a corresponding structure of amide type also by reacting it with a carboxylic acid in the presence of a suitable additive and condensing agent in an organic solvent such as DMF or dichloromethane.

The amino group or alkylamino group can be converted into a corresponding structure of urea type or thiourea type by reacting it with an isocyanate or an isothiocyanate in the presence of, if necessary, an organic base such as triethylamine, diusopropylethylamine, pyridine or N,N-dimethylaminopyridine in an organic solvent such as DMF, toluene or dichloromethane.

The product having the sulfonamide structure formed as described above can be alkylated by the above-described Mitsunobu reaction with an alcohol. The alkylation reaction can be carried out also by reacting the compound with an alkylating agent such as an alkyl halide or an alkyl sulfonate in the presence of a suitable base in an organic solvent.

It is possible that the phenylalanine derivatives represented by the general formula (1) in the present invention have optical isomers because they have an asymmetric carbon atom. The compounds of the present invention also include those optical isomers. Various tautomers of the phenylalanine derivatives of the general formula (1) are possible in the present invention because they contain movable hydrogen atoms. The compounds of the present invention also include those tautomers.

When the compounds of general formula (1) can form salts thereof, the salts are pharmaceutically acceptable ones. When the compound has an acidic group such as carboxyl group, the salts can be ammonium salts, or salts thereof with alkali metals, e.g. sodium and potassium, salts thereof with alkaline earth metals, e.g. calcium and magnesium, salts thereof with aluminum and zinc, salts thereof with organic amines, e.g. triethylamine, ethanolamine, morpholine, piperidine and dicyclohexylamine, and salts thereof with basic amino acids, e.g. arginine and lysine. When the compound has a basic group, the salts can be those with inorganic acids, e.g. hydrochloric acid, sulfuric acid and phosphoric acid; those with organic acids, e.g. acetic acid, citric acid, benizoic acid, maleic acid, fumaric acid, tartaric acid and succinic acid; and those with organosulfonic acids, e.g. methanesulfonic acid and p-toluenesulfonic acid. The salts can be formed by mixing a compound of the general formula (1) with a necessitated acid or base in a proper ratio in a solvent or dispersing agent or by the cation exchange or anion exchange reaction with another salt.

The compounds of the general formula (1) of the present invention also include solvates thereof such as hydrates and alcohol adducts thereof.

The compounds of general formula (1) and salts thereof are administered as they are or in the form of various medicinal compositions to patients. The dosage forms of the medicinal compositions are, for example, tablets, powders, pills, granules, capsules, suppositories, solutions, sugar-coated tablets, depots and syrups. They can be prepared with ordinary preparation assistants by an ordinary method.

For example, the tablets are prepared by mixing the phenylalanine derivative, the active ingredient of the present invention, with any of known adjuvants such as inert diluents, e.g. lactose, calcium carbonate and calcium phosphate; binders, e.g. acacia, corn starch and gelatin; extending agents, e.g. alginic acid, corn starch and pre-gelatinized starch; sweetening agents, e.g. sucrose, lactose and saccharin; corrigents, e.g. peppermint, Akamono (Gaultheria aderothrix) oil and cherry; lubricants, e.g. magnesium stearate, talc and carboxymethyl cellulose; excipients for soft gelatin capsules and suppositories, e.g. fats, waxes, semi-solid or liquid polyols, natural oils and hardened oils; and excipients for solutions, e.g. water, alcohols, glycerols, polyols, sucrose, inverted sugars, glucose and vegetable oils.

The antagonist containing one of the compounds of above general formula (1) or one of salts thereof as active ingredient is usable as a therapeutic agent or preventing agent for diseases in which $\alpha 4\beta 7$ integrin-depending adhesion process participates in the pathology, such as inflammatory bowel diseases, diabetes, tumor proliferation and tumor metastasis.

The dose of the compound of general formula (1) or salt thereof used for the above-described purpose varies depending on the intended therapeutic effect, administration method, period of the treatment, and age and body weight of the patient. The dose is usually 1 $\mu$g to 5 g a day for adults in the oral administration, and 0.01 $\mu$g to 1 g a day for adults in the parenteral administration.

EXAMPLES

The following Examples will further illustrate the present invention, which are only preferred embodiments of the invention and which by no means limit the invention.

Example 1

Preparation of Resin 3.0 g of Wang resin (0.87 mmol/g) was suspended in DMF, and the obtained suspension was left to stand at room temperature for 3 hours. The superfluous solvent was removed, and the rest was added to a solution of 4.4 g of N-(9-fluorenylmethoxycarbonyl)-O-(2,6-dichlorobenzyl)-L-tyrosine, 1.2 ml of 2,6-dichlorobenzoyl chloride and 1.2 ml of pyridine in 30 ml of DMF, and the resultant mixture was stirred at room temperature for 20 hours. The superfluous solvent was removed, and the resin was washed with 30 ml of DMF twice. The obtained resin was treated with 20% solution of piperidine in DMF at room temperature for 3 hours. The solvent was removed, and the residue was washed with 30 ml of each of DMF and dichloromethane 3 times each. The obtained resin was used for the subsequent reaction.

Example 2

N-(Trans-4-carboxycyclohexane-1-carbonyl)-O-(2,6-dichlorobenzyl)-L-tyrosine 30 mg of the resin obtained in Example 1 was added to a solution of 170 mg of trans-1,4-cyclohexanedicarboxylic acid, 140 mg of HOAt, 150 $\mu$l of DIC and 1.5 ml of DMF to conduct the reaction at room temperature for 20 hours. The reaction solution was removed and the remaining resin was washed with DMF, dichloromethane and ether 3 times each. The resin was treated with 95% trifluoroacetic acid for 1 hour. The resin was taken by the filtration and then washed with acetonitrile. The wash solutions were combined together, concentrated and purified by the reversed-phase HPLC [Inertsil ODS column, developer: water/acetonitrile (TFA 0.05%)] to obtain the intended compound.

Yield: 2.8 mg; MS (ESI, m/z): 494, 496, 498 [M+H]$^+$ [$C_{24}H_{25}Cl_2NO_6$: 493, 495, 497].

Example 3

N-(Trans-4-phenylhydrazinocarbonylcyclohexane-1-carbonyl)-O-(2,6-dichlorobenzyl)-L-tyrosine 30 mg of the resin obtained in Example 1 was added to a solution of 170 mg of trans-1,4-cyclohexanedicarboxylic acid, 140 mg of HOAt, 150 μl of DIC and 1.5 ml of DMF to conduct the reaction at room temperature for 20 hours. The reaction solution was removed and the remaining resin was washed with DMF twice, and added to a solution of 110 μl of phenylhydrazine, 140 mg of HOAt and 150 μl of DIC in 1.5 ml of DMF to conduct the reaction for 20 hours. The reaction solution was removed, and the resin was washed with DMF, dichloromethane and ether 3 times each. The resin was treated with 95% aqueous trifluoroacetic acid solution for 1 hour. The resin was taken by the filtration and then washed with acetonitrile. The wash solutions were combined together, concentrated and purified by the reversed-phase HPLC [Inertsil ODS column, developer: water/acetonitrile (TFA 0.05%)] to obtain the intended compound.

Yield: 2.1 mg; MS (ESI, m/z): 584, 586, 588 [M+H]$^+$ [$C_{30}H_{31}Cl_2N_3O_5$: 583, 585, 587].

Example 4

N-[Trans-4-(4-bromophenylhydrazinocarbonyl)cyclohexane-1-carbonyl]-O-(2,6-dichlorobenzyl)-L-tyrosine The same procedure as that of Example 3 was repeated except that the resin prepared in Example 1 and 4-bromophenylhydrazine were used to obtain the title compound.

Yield: 2.2 mg; MS (ESI, m/z): 662, 664, 666, 668 [M+H]$^+$ [$C_{30}H_{30}BrCl_2N_3O_5$: 661, 663, 665, 667].

Examples 5 to 9

The same procedure as that of Example 3 was repeated except that the resin prepared in Example 1 and a corresponding amine were used and that HPLC purification was omitted to obtain the compounds shown in Table 1.

D in Table 1 is a substituent in general formula (1-1) given below.

Examples 10 to 44

The same procedure as that of Example 3 was repeated except that the resin prepared in Example 1 and a corresponding amine or hydrazine were used. After the HPLC purification, the intended compounds were obtained. Refer to Table 1.

D in Table 1 is a substituent in general formula (1-1) given below.

TABLE 1

(1-1)

| Example | D | MS (ESI, m/z) measured value [M + H]+ |
|---|---|---|
| 5 | PhNH | 569, 571, 573 |
| 6 | PhCH2NH | 583, 585, 587 |
| 7 | cHexyl-NH | 575, 577, 579 |
| 8 | n-Butyl-NH | 549, 551, 553 |
| 9 | 1-Piperidyl | 561, 563, 565 |
| 10 | partial structure 1 | 604, 606, 608 |
| 11 | partial structure 2 | 563, 565, 567 |
| 12 | partial structure 3 | 533, 535, 537 |
| 13 | partial structure 4 | 575, 577, 579 |
| 14 | partial structure 5 | 614, 616, 618 |
| 15 | partial structure 6 | 508, 510, 512 |
| 16 | partial structure 7 | 551, 553, 555 |
| 17 | partial structure 8 | 536, 538, 540 |
| 18 | partial structure 9 | 591, 593, 595 |
| 19 | partial structure 10 | 563, 565, 567 |
| 20 | partial structure 11 | 579, 581, 583 |
| 21 | partial structure 12 | 562, 564, 566 |
| 22 | partial structure 13 | 604, 606, 608 |
| 23 | partial structure 14 | 522, 524, 526 |
| 24 | partial structure 15 | 655, 657, 659 |
| 25 | partial structure 16 | 648, 650, 652 |
| 26 | partial structure 17 | 669, 671, 673 |
| 27 | partial structure 18 | 604, 606, 608 |
| 28 | partial structure 19 | 577, 579, 581 |
| 29 | partial structure 20 | 590, 592, 594 |
| 30 | partial structure 21 | 585, 587, 589 |
| 31 | partial structure 22 | 612, 614, 616 |
| 32 | partial structure 23 | 603, 605, 607 |
| 33 | partial structure 24 | 609, 611, 613 |
| 34 | partial structure 25 | 598, 600, 602 |
| 35 | partial structure 26 | 668, 670, 672 |
| 36 | partial structure 27 | 590, 592, 594 |
| 37 | partial structure 28 | 598, 600, 602 |
| 38 | partial structure 29 | 576, 578, 580 |
| 39 | partial structure 30 | 643, 645, 647 |
| 40 | partial structure 31 | 578, 580, 582 |
| 41 | partial structure 32 | 615, 617, 619 |
| 42 | partial structure 33 | 583, 585, 587 |
| 43 | partial structure 34 | 550, 552, 554 |
| 44 | partial structure 35 | 614, 616, 618 |
| (cHex = Cyclohexyl) | | |

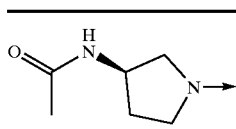

partial structure 1

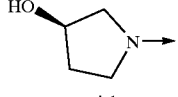

partial structure 2

TABLE 1-continued
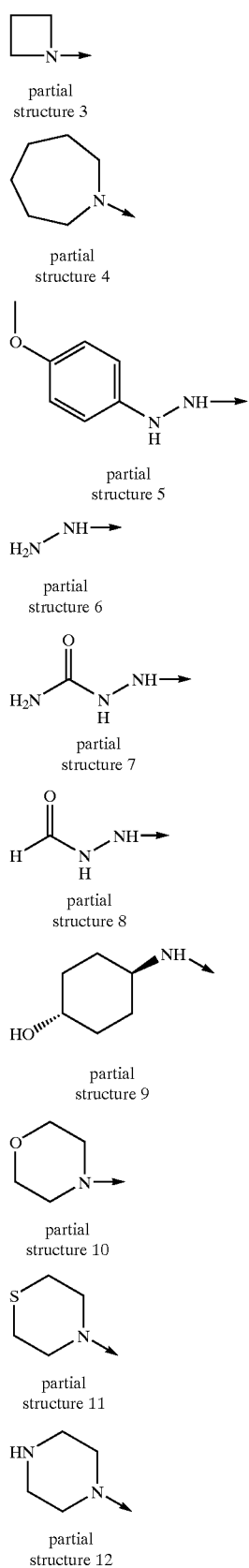
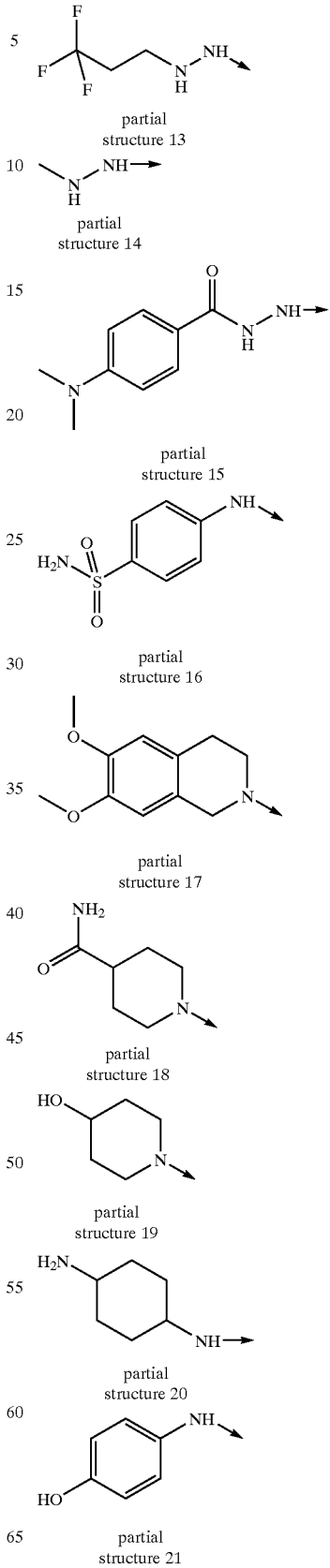

TABLE 1-continued

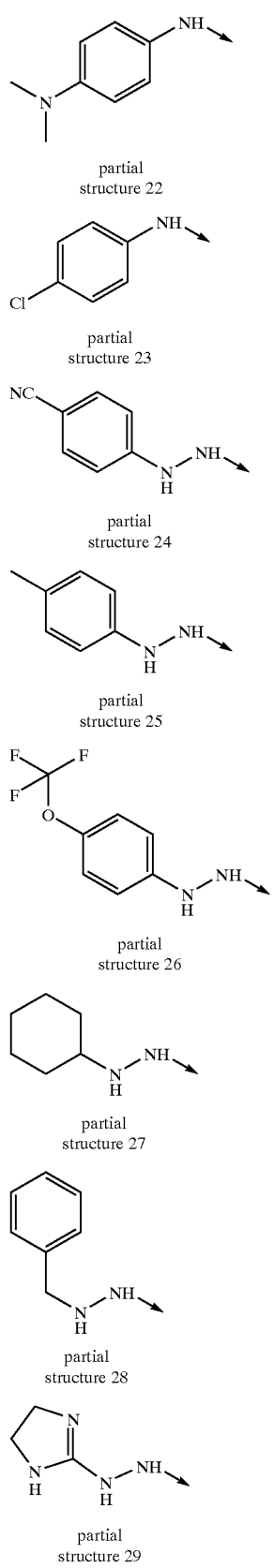

partial structure 22 partial structure 23 partial structure 24 partial structure 25 partial structure 26 partial structure 27 partial structure 28 partial structure 29

TABLE 1-continued

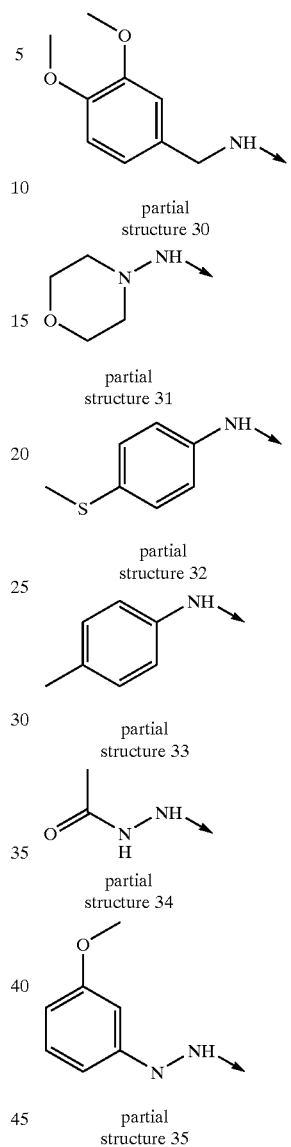

partial structure 30 partial structure 31 partial structure 32 partial structure 33 partial structure 34 partial structure 35

Example 45

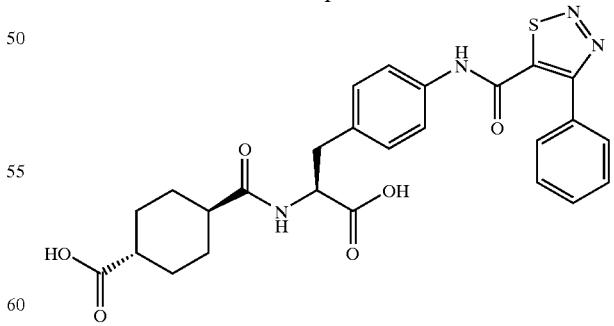

N-(Trans-4-carboxycyclohexane-1-carbonyl)-4-{[(4-phenyl-1,2,3-thiadiazole-5-yl)carbonyl]amino}-L-phenylalanine Step 1 Attachment of Amino Acid to Resin:

2.03 g of Wang resin (0.76 mmol/g) was alternately washed with NMP and DCM twice and then with NMP three times. A solution (11 ml) of 2.00 g of Fmoc-Phe(4-nitro)-OH in NMP, a solution (5 ml) of 0.87 ml of pyridine in NMP and a solution (4 ml) of 0.66 ml of 2,6-dichlorobenzoyl chloride in NMP were successively added to the resin, and the obtained mixture was stirred at room temperature for 16 hours. The reaction solution was removed, and the resin was washed with DMF 3 times, with ethanol 3 times, with DCM 3 times and with NMP 3 times. NMP (7 ml), a solution (7 ml) of 1.49 ml of pyridine in NMP and a solution (7 ml) of 1.46 ml of acetic anhydride in NMP were added to the obtained resin. After stirring at room temperature for 2 hours, the reaction solution was removed, and the residue was washed with DMF 3 times, with ethanol 3 times and with DCM 3 times. The obtained resin was dried under reduced pressure.

Step 2 Reaction for Reducing Nitro Group:

530.0 mg (corresponding to 307 μmol) of the resin obtained in step 1 was added to 7.67 ml of 2 M solution of stannic chloride dihydrate (NMP:EtOH=20:1) to conduct the reaction at room temperature for 3 hours. The reaction solution was removed, and the residue was washed with DMF, ethanol and DCM 3 times each.

Step 3 Acylation Reaction:

The resin obtained in step 2 was washed with DMF 3 times. A solution (1.5 ml) of 190.2 mg (922 μmol) of 4-phenyl-1,2,3-thiadiazole-5-carboxylic acid in DMF (1.5 ml), a solution (2 ml) of 479.8 mg of PyBOP in DMF, a solution (1.23 ml) of 207.7 mg of HOBt in DMF and a solution (2 ml) of 321.3 μl of DIEA in DMF were successively added to the resin, and they were stirred at room temperature for 19.5 hours. The reaction solution was removed, and the residue was washed with DMF, ethanol, DCM and DMF 3 times each.

Step 4: Fmoc-removing Reaction:

5 ml of 20% solution of piperidine in DMF was added to the resin obtained as described above, and they were stirred for 5 minutes. The reaction solution was removed, 5 ml of 20% solution of piperidine in DMF was added again to the residue, and they were stirred for 15 minutes. The reaction solution was removed, and the resin was washed with DMF 3 times, with ethanol 3 times, with DCM 3 times, and again with NMP 3 times.

Step 5 Acylation Reaction:

A solution (2.2 ml) of 529 mg of trans-1,4-cyclohexanedicarboxylic acid in NMP and a solution (2.2 ml) of 418 mg of HOAt and 476 μl of DIC in NMP were successively added to the resin obtained in step 4. After stirring at room temperature for 4 hours, the reaction solution was removed, and the resin was washed with DMF, EtOH and DCM 3 times each.

Step 6 Cleavage from Resin:

95% aqueous trifluoroacetic acid solution (5 ml) was added to the resin obtained in step 5, and they were stirred for 1 hour and then filtered. 95% aqueous trifluoroacetic acid solution (5 ml) was added to the resin, and they were stirred for 1 hour and then filtered. The filtrates were combined together and then concentrated. After the purification by the reversed-phase HPLC [Symmetry C18 column (5 μm; 19 mm φ×50 mm) of Waters Co., developer: water/acetonitrile (TFA 0.05%)], the product was freeze-dried to obtain 69.2 mg of the intended compound.

MS (ESI, m/z): 523 [M+H]$^+$, 521 [M−H]$^-$, 635 [M+TFA−H]$^-$ [$C_{26}H_{26}N_4O_6S$: 522].

Example 46

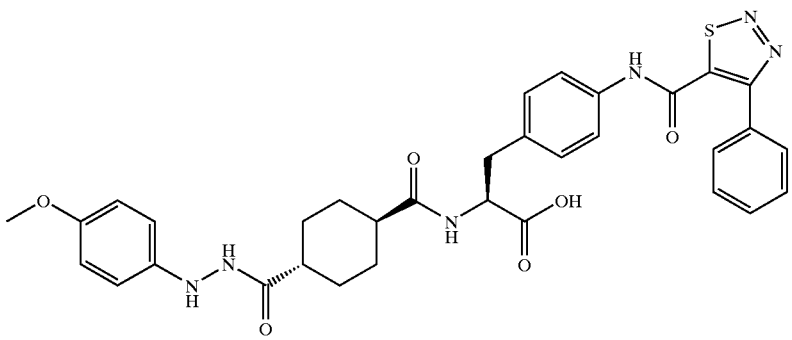

N-[Trans-4-(4-methoxyphenylhydrazinocarbonyl) cyclohexane-1-carbonyl]-4-{[(4-phenyl-1,2,3-thiadiazole-5-yl)carbonyl]amino}-L-phenyl-alanine Step 1 Conversion into Hydrazide:

414 mg of p-methoxyphenylhydrazine hydrochloride and a solution of 414 μl of DIEA in NMP (1.8 ml) were added to the resin (corresponding to 238 μmol) obtained in step 5 in Example 45, and then 323 mg of HOAt and a solution (1.8 ml) of 368 μl of DIC in NMP were added to the obtained mixture, and they were stirred at room temperature for 20 hours. The reaction solution was removed, and the residue was washed with DMF, ethanol and DCM 3 times each. The obtained resin was dried under reduced pressure.

Step 2 Cleavage from Resin:

80% aqueous trifluoroacetic acid solution (5 ml) was added to the resin obtained in step 1, and they were stirred for 1 hour and then filtered. 80% aqueous trifluoroacetic acid solution (5 ml) was added to the resin, and they were stirred for 1 hour and then filtered. The filtrates were combined together and then concentrated. After the purification by the reversed-phase HPLC [Symmetry C18 column (5 μm; 19 mm φ×50 mm) of Waters Co., developer: water/acetonitrile (TFA 0.05%)], the product was freeze-dried to obtain 24.2 mg of the intended compound.

MS (ESI, m/z): 643 [M+H]$^+$, 641[M+H]$^+$, 755[M+TFA−H]$^-$ [$C_{33}H_{34}N_6O_6S$: 642].

Example 47

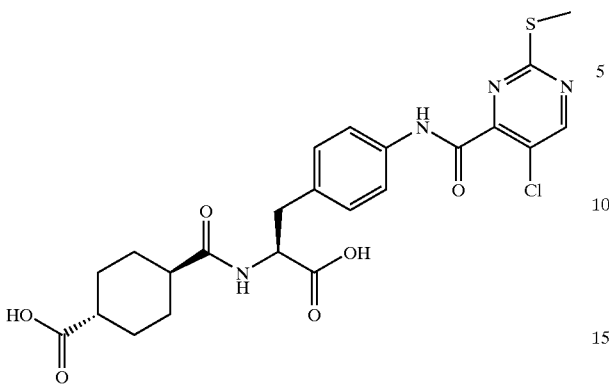

N-(Trans-4-carboxycyclohexane-1-carbonyl)-4-({[5-chloro-2-(methylsulfanil)pyrimidine-4-yl]carbonyl}amino)-L-phenylalanine 68.0 mg of the intended title compound was obtained from the resin (corresponding to 238 μmol) obtained in Step 2 in Example 45 in the same manner as that in step 3 and thereafter in Example 45 except that 4-phenyl-1,2,3-thiadiazole-5-carboxylic acid was replaced with 5-chloro-2-(methylthio)pyrimidine-4-carboxylic acid.

MS (ESI, m/z) 521 [M+H]$^+$, 633 [M+TFA−H]$^-$ [$C_{23}H_{25}ClN_4O_6S$: 520].

Example 48

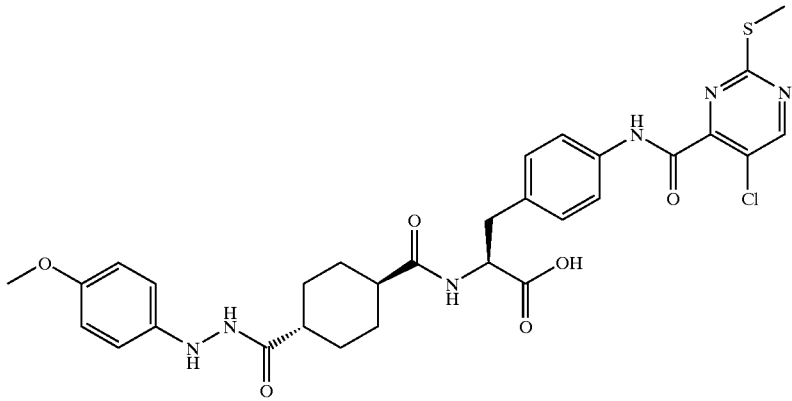

N-[Trans-4-(4-methoxyphenylhydrazinocarbonyl)cyclohexane-1-carbonyl]-4-({[5-chloro-2-(methylsulfanyl)pyrimidine-4-yl]carbonyl}-amino)-L-phenylalanine The acylation was conducted in the same manner as that in Step 3 in Example 45 except that 5-chloro-2-(methylthio)pyrimidine-4-carboxylic acid was used in the same manner as that in Example 47. Then the same procedure as that in Steps 4 and 5 in Example 45 was repeated to obtain a resin (corresponding to 232 μmol). From the resin, 19.4 mg of the intended title compound was obtained in the same manner as that in Step 1 and thereafter in Example 46.

MS (ESI, m/z) 641 [M+H]$^+$, 753 [M+TFA−H]$^-$ [$C_{30}H_{33}ClN_6O_6S$: 640].

Example 49

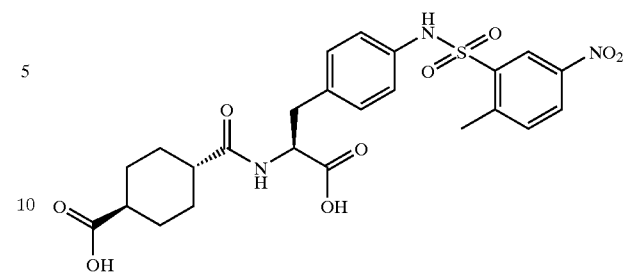

N-(Trans-4-carboxycyclohexane-1-carbonyl)-4-{[(2-methyl-5-nitrophenyl)-sulfonyl]amino}-L-phenylalanine Step 1 Preparation of Resin:

A solution of Fmoc-Phe(4-nitro)-OH (2.5 g), 2,6-dichlorobenzoyl chloride (0.745 ml) and pyridine (1.5 ml) in NMP (25 ml) was added to Wang resin (0.76 mmol/g, 2.3 g), and they were stirred at room temperature for 16 hours. The superfluous solvent was removed, and the resin was washed with DMF 3 times, with dichloromethane 3 times and with NMP twice. For capping unreacted hydroxyl group on the resin, the resin was treated with acetic acid anhydride (20 ml), pyridine (20 ml) and NMP (20 ml) for 2 hours. The superfluous solvent was removed, and the resin was washed with DMF 3 times and with dichloromethane 3 times and then dried under reduced pressure.

Step 2 Reduction of Nitro Group:

A solution of stannic chloride dehydrate (15.0 g) in NMP (30 ml) EtOH (1.5 ml) was added to 1.5 g of the resin obtained in step 1 to conduct the reaction at room temperature for 16 hours. The reaction solution was removed, and the residue was washed with NMP and dichloromethane 3 times each, and then dried under reduced pressure.

Step 3 Sulfonamidation:

500 mg of the resin obtained in step 2 was added to a solution of 400 mg of 2-methyl-5-nitrobenzenesulfonyl chloride, 800 μl of 2,6-lutidine and 15 ml of dichloromethane to conduct the reaction at 0° C. for 24 hours. The reaction solution was removed, and the resin was washed with dichloromethane, NMP and dichloromethane 3 times each, and then dried under reduced pressure.

Step 4: Removal of Fmoc Group:

20% piperidine solution (25 ml) was added to the resin obtained in step 3 to conduct the reaction for 10 minutes. The solvent was removed. 20% solution (25 ml) of piperidine in NMP was added to the obtained residue to conduct the reaction for 10 minutes. The solvent was removed, and the residue was washed with NMP and dichloromethane 3 times each and then dried under reduced pressure.

Step 5 Acylation Reaction:

500 mg of the resin obtained in step 4 was added to a solution of 170 mg of trans-1,4-cyclohexanedicarboxylic acid, 140 mg of HOAt, 150 μl of DIC and 1.5 ml of DMF to conduct the reaction at room temperature for 20 hours. The reaction solution was removed, and the resin was washed with DMF, dichloromethane and ether 3 times each.

Step 6 Cleavage from Resin:

The resin obtained in step 5 was treated with 95% aqueous trifluoroacetic acid for 1 hour, then taken by the filtration and washed with acetonitrile. The wash solutions were combined together and then concentrated. After the purification of a part of the product by the reversed-phase HPLC [developer: water/acetonitrile (TFA 0.05%)], the intended compound was obtained.

Yield: 15.0 mg; MS (ESI, m/z): 534 [M+H]$^+$ [$C_{24}H_{27}N_3O_9S$: 533].

Example 50

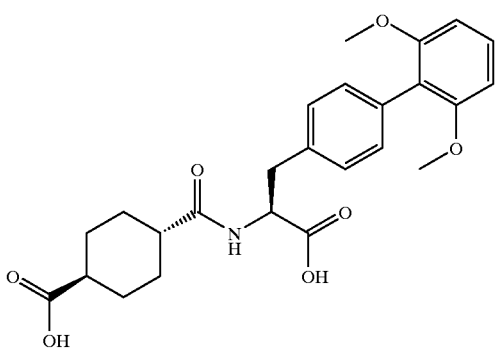

N-(Trans-4-carboxycyclohexane-1-carbonyl)-4-(2,6-dimethoxyphenyl)-L-phenylalanine Step 1 Synthesis of the Following Compound:

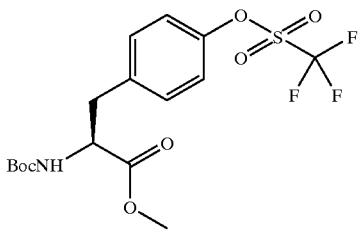

Boc-Tyr-OMe (15.1 g, 50.8 mmol) was dissolved in methylene chloride (70 ml). 20.6 ml of pyridine was added to the obtained solution. Anhydrous trifluoromethane-sulfonic acid (9.41 ml, 55.9 mmol) was added dropwise to the obtained mixture at 0° C. They were stirred at 0° C. for 1 hour and then diluted with 100 ml of methylene chloride. After washing with saturated aqueous ammonium chloride solution (100 ml) and then with water (100 ml×2), the organic layer was dried over anhydrous sodium sulfate and then concentrated under reduced pressure to obtain 21.9 g (100%) of the intended compound.

$^1$H-NMR (CDCl$_3$) δ=1.43 (9H, s), 3.05 (1H, dd, J=6.6, 14.0 Hz), 3.19 (1H, dd, J=5.7, 14.0 Hz), 3.73 (3H, s), 4.59–4.65 (1H, m), 5.03 (1H, d, J=6.9 Hz), 7.20–7.27 (4H, m).

Step 2 Synthesis of the Following Compound:

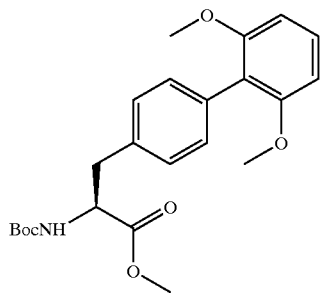

The compound obtained in step 1 (9.80 g, 22.9 mmol) was dissolved in DME (170 ml) under argon atmosphere. Potassium carbonate (12.6 g, 91.6 mmol), 2,6-dimethoxyphenylboronic acid (5.01 g, 27.5 mmol) and tetrakis(triphenylphosphine) palladium (O) (2.65 g, 2.29 mmol) were added to the obtained solution. The reaction mixture was stirred at 70° C. for 6 hours and then dissolved in water (150 ml). After extracting with ethyl acetate (150 ml×3), the organic layers were combined together, dried over anhydrous sodium sulfate and concentrated under reduced pressure. The residue was purified by the silica gel column chromatography (hexane, hexane/ethyl acetate, 10/1, 8/1, 6/1) to obtain 8.64 g (91%) of the intended compound.

$^1$H-NMR (CDCl$_3$) δ=1.55 (9H, s), 3.09–3.16 (2H, m), 3.72 (6H, s), 3.74 (3H, s), 4.59–4.66 (1H, m), 5.01–5.06 (1H, m), 6.65 (2H, d, J=8.7 Hz), 7.15–7.30 (5H, m).

Step 3 Synthesis of Methyl 4-(2,6-Dimethoxyphenyl)-L-phenylalanilne Hydrochloride:

The compound obtained in step 2 (8.64 g, 20.8 mmol) was dissolved in 4 N hydrochloric acid/ethyl acetate solution (100 ml), and the obtained solution was stirred for 4 hours. Crystals thus precipitated were taken by the filtration and then washed with ethyl acetate. The crystals were dried to obtain 7.01 g (96%) of the intended compound in the form of white crystals.

$^1$H-NMR (CDCl$_3$) δ=3.47 (2H, t, J=5.4 Hz), 3.71 (6H, s), 3.81 (3H, s), 4.43 (1H, t, J=5.4 Hz), 6.63 (2H, d, J=8.4 Hz), 7.24–7.35 (5H, m), 8.73 (2H, br s). MS:ESI$^+$316 [M+H]$^+$; [$C_{18}H_{21}NO_4$·HCl: 315 36.5].

Step 4 Synthesis of the Following Compound:

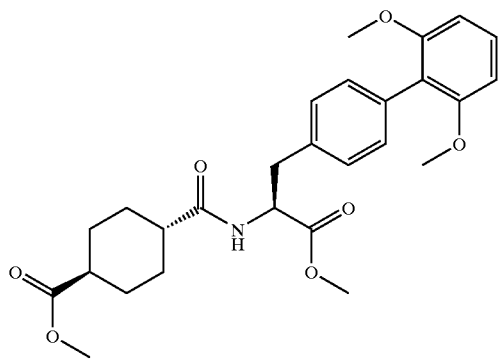

Trans-1,4-cyclohexanedicarboxylic acid (34.4 mg, 0.2 mmol) and HOAt (81.6 mg, 0.6 mmol) were dissolved in NMP (1 ml). DICD(0.93 ml, 0.6 mmol) was added to the obtained solution. They were stirred at room temperature for 2 hours. A solution (0.5 ml) of methyl 4-(2,6-dimethoxyphenyl)-L-phenylalanine hydrochloride (35.2 mg, 0.1 mmol) and DIEA (0.0176 ml, 0.1 mmol) in NMP was added dropwise to the obtained mixture. They were stirred for additional 3 hours. Methanol (0.5 ml) was added to the obtained mixture and they were stirred for 20.5 hours. Saturated aqueous sodium hydrogencarbonate solution was added to the reaction mixture. After the extraction with hexane/ethyl acetate (1/1), the extract was concentrated under reduced pressure. The residue was purified by the silica gel column chromatography (hexane, hexane/ethyl acetate, 3/1 to 1/1) to obtain 48.2 mg of the intended compound, which was used for the subsequent reaction.

MS (ESI, m/z): 484 [M+H]$^+$ [$C_{27}H_{33}NO_7$: 483].

Step 5 Synthesis of N-(Trans-4-carboxycyclohexane-1-carbonyl)-4-(2,6-dimethoxyphenyl)-L-phenylalanine:

The compound (48.2 mg, 0.10 mmol) obtained in step 4 was dissolved in methanol/THF (0.5 ml/0.5 ml). 0.1 M aqueous LiOH solution (2.2 ml, 0.22 mmol) was added to the obtained solution. After stirring for 2 hours, 0.1 M aqueous LiOH solution (0.2 ml) was added to the obtained mixture, and they were stirred for 17.5 hours. Water and dichloromethane were added to the reaction solution. The aqueous layer thus formed was taken and adjusted to pH 1 with 1 N hydrochloric acid. After the extraction with dichloromethane/isopropanol (2/1), the extract was dried over anhydrous sodium sulfate and then concentrated under reduced pressure. The residue was purified by the silica gel column chromatography (chloroform/methanol 10/1, 2/1) to obtain 32.9 mg of the intended compound.

LC-MS: ESI$^+$456 [MH]$^+$ [$C_{25}H_{29}NO_7$: 455].

Example 51

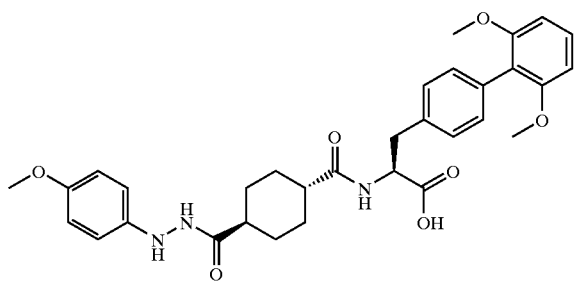

N-[Trans-4-(4-methoxyphenylhydrazinocarbonyl)cyclohexane-1-carbonyl]-4-(2,6-dimethoxyphenyl)-L-phenylalanine Step 1 Synthesis of N-[(9H-Fluorene-9-ylmethoxy)carbonyl]-4-(2,6-dimethoxyphenyl)-L-phenylalanine:

Methyl 4-(2,6-dimethoxyphenyl)-L-phenylalanine hydrochloride (3.53 g, 10 mmol) obtained in step 3 in Example 50 was dissolved in methanol/THF. A solution of LiOH (927 mg) in water (10 ml) was added to the obtained solution. After stirring for 40 minutes, the reaction solution was filtered, and the filtrate was concentrated under reduced pressure and then subjected to the azeotropic distillation with ethanol twice. The obtained solid was dissolved in acetone/water (20 ml/20 ml). Sodium hydrogencarbonate (1.68 g) and Fmoc-Osu (3.37 g) were added to the obtained solution, and they were stirred for 19 hours. The reaction solution was adjusted to pH 2 with concentrated hydrochloric acid. After the extraction with a solvent mixture of isopropanol/dichloromethane (1/1), the extract was concentrated under reduced pressure. The product was purified by the silica gel column chromatography (hexane, hexane/ethyl acetate, 2/1, 3/2) to obtain 5.74 g (100%) of the intended compound.

Step 2 Preparation of Resin:

A solution of N-(9-fluorenylmethyloxycarbonyl)-4-(2,6-dimethoxyphenyl)-L-phenylalanine (5.24 g), DIC (1.55 ml) and DMAP (61.1 mg) in DMF (40 ml) was added to Wang resin (0.76 mmol/g, 6.58 g), and they were stirred at room temperature for 27 hours. The superfluous solvent was removed, and the resin was washed with DMF 8 times, with dichloromethane 8 times and with DMF 8 times. For capping unreacted hydroxyl group on the resin, the resin was treated with acetic acid anhydride (4.25 ml), pyridine (3.64 ml) and DMF (22 ml) for 2 hours. The superfluous solvent was removed, and the resin was washed with DMF 7 times, with methanol 7 times, with dichloromethane 7 times and with DMF 5 times.

Step 3: Removal of Fmoc Group:

40% piperidine solution (20 ml) was added to the resin obtained in step 2 to conduct the reaction for 5 minutes. The solvent was removed. 40% solution (20 ml) of piperidine in NMP was added to the obtained residue to conduct the reaction for 20 minutes. The solvent was removed, and the residue was washed with NMP, methanol and dichloromethane 8 times each and then dried under reduced pressure.

Step 4 Acylation Reaction:

1.6 g of the resin obtained in step 3 was stirred in a solution of 2.1 g of trans-1,4-cyclohexanedicarboxylic acid, 1.66 g of HOAt and 1.89 ml of DIC in 16 ml of NMP at room temperature for 20 hours. The reaction solution was removed, and the resin was washed with DMF, dichloromethane, DMF and dichloromethane 3 times each, and then with NMP once. 2.13 g of 4-methoxyphenylhydrazine hydrochloride, 1.89 ml of DIC, 1.66 g of HOAt and a solution of 2.13 ml of diisopropylethylamine in 16 ml of NMP were added to the resin, and they were stirred at room temperature for 16 hours. The reaction solution was removed, and the resin was washed with DMF, dichloromethane, DMF and dichloromethane 3 times each, and with methanol and ether once each.

Step 5 Cleavage from Resin:

The resin obtained in step 4 was treated with 80% trifluoroacetic acid for 2 hours. The resin was taken by the filtration and then washed with acetonitrile. The wash solutions were combined together and concentrated. After the purification by the reversed phase HPLC (developer: water, acetonitrile (TFA 0.05%)), the intended compound was obtained.

Yield: 17.1 mg; MS (ESI, m/z): 576 [M+H]$^+$ [$C_{32}H_{37}N_3O_7$: 575].

Example 52

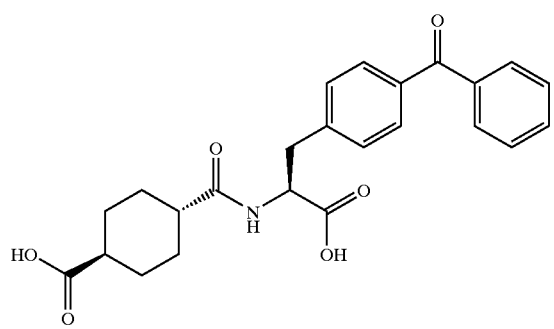

N-(Trians-4-carboxycyclohexane-1-carbonyl)-4-(phenylcarbonyl)-L-phenyl-alanine

Step 1 Preparation of Resin:

0.43 g of Wang resin (0.76 mmol/g) was washed with DMF. A solution of three reagents, i.e. 0.416 g (2.5 eq) of Fmoc-Phe(4-benzoyl)-OH, 0.128 ml (2.5 eq) of DIC and 0.004 g (0.1 eq) of DMAP, in DMF (3.6 ml ) was added to the resin, and they were stirred at room temperature for 4 hours. The reaction solution was removed, and the resin was washed with DMF twice, with DCM twice, with DMF twice, with DCM twice and with DMF twice. DMF (3.3 ml) and then 0.264 ml (10 eq) of pyridine and 0.309 ml (10 eq) of acetic acid anhydride were added to the obtained resin. They were stirred at room temperature for 2 hours and then the reaction solution was removed. The residue was washed with DMF, DCM, DMF, DCM, methanol and ether. The obtained resin was dried under reduced pressure.

Step 2 Removal of Fmoc Group:

0.03 g of the resin obtained in step 1 was washed with DMF. 1.5 ml of 20% solution of piperidine in DMF was added to the resin, and they were stirred for 3 minutes. The reaction solution was removed, 1.5 ml of 20% solution of piperidine in DMF was added to the residue, and they were stirred for 10 minutes. The reaction solution was removed, and the resin was washed with DMF twice, with DCM twice and again with DMF twice.

Step 3 Acylation Reaction:

400 mg of the resin obtained in step 2 was stirred in a solution of 489 mg of trans-1,4-cyclohexanedicarboxylic acid, 387 mg of HOAt and 0.44 ml of DIC in 4 ml of NMP at room temperature for 1 hour. The reaction solution was removed, and the resin was washed with DMF, dichloromethanie, DMF and dichloromethane 3 times each, and with methanol and ether once each.

Step 4 Cleavage from Resin:

The resin obtained in step 3 was treated with 95% trifluoroacetic acid for 2 hours. The resin was taken by the filtration and then washed with acetonitrile. The wash solutions were combined together. After the purification by the reversed phase HPLC (developer: water, acetonitrile (TFA 0.05%)), the intended compound was obtained.

Yield: 11.4 mg; MS (EST, m/z): 424 [M+H]$^+$ [$C_{24}H_{25}NO_6$: 423]

(Test Example) VCAM Antagonistic Activity (VCAM-1/ $\alpha 4\beta 1$ Binding Assay):

The capacity of a test substance antagonistic to the binding of cell strain Jurkat (ATCC TIB-152) of human T cells, known to express integrin $\alpha 4\beta 1$, with VCAM-1 was determined. 100 µl/well of a solution (500 ng/ml ) of recombinant human VCAM-1 (R & D systems) diluted with buffer A (0.1 M $NaHCO_3$, pH 9.6) was added to a micro titer plate having 96 wells (Nunc Maxisorp). After the incubation at 4° C. overnight, unbound VCAM-1 was removed by once washing with PBS. After completion of the washing, a buffer (buffer B) obtained by diluting Block Ace® (Dainippon Pharmaceutical Co., Ltd.) with PBS to 1/4 concentration was added in an amount of 150 µl /well. After the incubation at room temperature for 1 hour, buffer B was removed and the plate was washed with PBS once.

Jurkat cells were washed with Dulbecco modified Eagle medium (SIGMA, hereinafter referred to as "DMEM") twice and then incubated in DMEM containing 10 µg/ml of Calcein-AM (Wako Pure Chemical Industries, Ltd.) at 37° C. in dark place for 30 minutes to label them with fluorescence. The cells were again suspended in a binding buffer (DMEM containing 20 mM HEPES, 0.1% BSA).

50 µl of a test substance of various concentrations obtained by the dilution with the binding buffer was added to the plate. Immediately thereafter, 50 µl (final volume: 100 µl/well) of the fluorescent Jurkat cells (4×10$^6$ cells/ml ) were added thereto, and they were incubated at room temperature for 30 minutes. After the shaking on a plate shaker (IKA MTS-4) at 800 rpm for 30 seconds, the solution was immediately removed to remove the unbound cells. The fluorescence quantity of the bound cells remaining in the wells was determined with a fluorescent plate reader (Wallac 1420 ARVO multi-label counter) (filter excitation wave length: 485 nm, emission wave length: 535 nm). The fluorescent strength thus obtained is proportional to the number of Jurkat cells bound to VCAM-1 and remaining on the plate. The binding rate of each test material in various concentrations was determined while the fluorescent strength of the test material-free well was determined to be 100%. The concentration IC$_{50}$ for the 50% binding inhibition was calculated.

The obtained test results are shown in Table 2. The activities were classified into group A wherein IC$_{50}$ was 0.2 µmol/l or below, group B wherein IC$_{50}$ was higher than 0.2 µmol/l and not above 1 µmol/l, group C wherein IC$_{50}$ was higher than 1 µmol/l and not above 5 µmol/l, group D wherein IC$_{50}$ was higher than 5 µmol/l and not above 25 µmol/l, and group E wherein IC$_{50}$ was higher than 25 µmol/l and not above 50 µmol/l.

(Test Example) VCAM Antagonistic Activity (VCAM-1/ $\alpha 4\beta 7$ Binding Assay):

The capacity of a test substance antagonistic to the binding of lymphoma cell strain RPMI-8866 of human B cells, known to express integrin $\alpha 4\beta 7$, with VCAM-1 was determined.

100 µl/well of a solution (500 ng/ml ) of recombinant human VCAM-1 (R & D systems) diluted with buffer A (0.1 M $NaHCO_3$, pwH 9.6) was added to a micro titer plate having 96 wells (Nunc Maxisorp). After the incubation at 4° C. overnight, unbound VCAM-1 was removed by once washing with PBS. After completion of the washing, a buffer (buffer B) obtained by diluting Block Ace® (Dainippon Pharmaceutical Co., Ltd.) with PBS to 1/4 concentration was added in an amount of 150 µl/well. After the incubation at room temperature for 1 hour, buffer B was removed and the plate was washed with PBS once.

RPMI-8866 cells were incubated in Dulbecco modified Eagle medium containing 10 µg/ml of Calcein-AM (Wako Pure Chemical Industries, Ltd.) (SIGMA, hereinafter referred to as "DMEM") at 37° C. for 30 minutes to label them with fluorescence. The cells were again suspended in a binding buffer (DMEM containing 20 mM HEPES, 0.1% BSA) containing 4 mM of $MnCl_2$.

50 µl of a test substance of various concentrations obtained by the dilution with the binding buffer was added to the plate. Immediately thereafter, 50 µl (final volume: 100 µl/well) of the fluorescent RPMI-8866 cells (4×10$^6$ cells/ml) were added thereto, and they were incubated at room temperature for 30 minutes. After the shaking on a plate shaker (IKA MTS-4) at 800 rpm for 30 seconds, the solution was immediately removed to remove the unbound cells. The fluorescence quantity of the bound cells remaining in the wells was determined with a fluorescent plate reader (Wallac 1420 ARVO multi-label counter) (filter excitation wave length: 485 nml, emission wave length: 535 nm). The fluorescent strength thus obtained is proportional to the number of RPMI-8866 cells bound to VCAM-1 and remaining on the plate. The binding rate of each test material in various concentrations was determined while the fluorescent strength of the test material-free well was determined to be 100%. The concentration IC$_{50}$ for the 50% binding inhibition was calculated.

The obtained test results are shown in Table 2. The activities were classified into group A wherein IC$_{50}$ was 0.2 µmol/l or below, group B wherein IC$_{50}$ was higher than 0.2 µmol/l and not above 1 µmol/l, group C wherein IC$_{50}$ was higher than 1 µmol/l and not above 5 µmol/l, group D wherein IC$_{50}$ was higher than 5 μmol/l and not above 25 μmol/l, and group E wherein IC$_{50}$ was higher than 25 μmol/l and not above 50 μmol/l.

(Test Example) Rat MAdCAM-1 Antagonistic Activity (rat MAdCAM-1/α4β7 Binding Assay):

The capacity of a test substance antagonistic to the binding of lymphoma cell strain RPMI-8866 of human B cells, known to express integrin α4β7, with rat MAdCAM-1/human IgG1 chimera protein was determined.

100 μl/well of human IgG1 antibody (SIGMA #I-6260) diluted with buffer A to 1/1,000 concentration was added to a micro titer plate having 96 wells. After the incubation at 4° C. overnight, the plate was washed with PBS once. 100 μl/well of rat MAdCAM-1/human IgG1 chimera protein solution diluted with a buffer (buffer C)obtained by diluting Block Ace® (Dainippon Pharmaceutical Co., Ltd.) with PBS to 1/10 concentration was added in an amount of 100 μl/well. After the incubation at 37° C. for 2 hours, unbound MAdCAM-1/IgG was removed by washing once with PBS. After completion of the washing, 150 μl/well of buffer B was added and the incubation was continued at room temperature for 1 hour. Buffer B was removed and then the plate was washed with PBS once.

RPMI-8866 cells were incubated in DMEM containing 10 μg/ml of Calcein-AM at 37° C. for 30 minutes to label them with fluorescence. The cells were again suspended in a binding buffer containing 4 mM of MnCl$_2$.

50 μl of a test substance of various concentrations obtained by the dilution with the binding buffer was added to the plate. Immediately thereafter, 50 μl (final volume: 100 μl/well) of the fluorescent RPMI-8866 cells (4×10$^6$ cells/ml) were added thereto, and they were incubated at room temperature for 30 minutes. After the shaking on a plate shaker (IKA MTS-4) at 800 rpm for 30 seconds, the solution was immediately removed to remove the unbound cells. The fluorescence quantity of the bound cells remaining in the wells was determined with a fluorescent plate reader (Wallac 1420 ARVO multi-label counter). The fluorescence strength thus obtained is proportional to the number of RPMI-8866 cells bound to MAdCAM-1 and remaining on the plate. The binding rate of each test material in various concentrations was determined while the fluorescent strength of the test material-free well was determined to be 100%. The concentration IC$_{50}$ for the 50% binding inhibition was calculated.

The obtained test results are shown in Table 2. The activities were classified into group A wherein IC$_{50}$ was 0.2 μmol/l or below, group B wherein IC$_{50}$ was higher than 0.2 μmol/l and not above 1 μmol/l, group C wherein IC$_{50}$ was higher than 1 μmol/l and not above 5 μmol/l, group D wherein IC$_{50}$ was higher than 5 μmol/l and not above 25 μmol/l, and group E wherein IC$_{50}$ was higher than 25 μmol/l and not above 50 μmol/l.

TABLE 2

Results of the determination of antagonistic activity to integrin (IC50, μ mol/L): 50 ≥ E ≥ 25 ≥ D ≥ 5 ≥ C ≥ 1 ≥ B ≥ 0.2 ≥ A

| Ex. | MadCAM/α 4 β 7 | VCAM/α 4 β 7 | VCAM/α 4 β 1 |
|---|---|---|---|
| 2 | A | A | D |
| 3 | B | A | E |
| 4 | B | B | E |
| 6 | C | C | E |
| 14 | B | A | C |
| 33 | C | A | D |
| 34 | B | A | C |
| 35 | C | A | E |
| 44 | B | A | D |

TABLE 2-continued

Results of the determination of antagonistic activity to integrin (IC50, μ mol/L): 50 ≥ E ≥ 25 ≥ D ≥ 5 ≥ C ≥ 1 ≥ B ≥ 0.2 ≥ A

| Ex. | MadCAM/α 4 β 7 | VCAM/α 4 β 7 | VCAM/α 4 β 1 |
|---|---|---|---|
| 45 | C | A | C |
| 46 | C | A | D |
| 50 | C | A | C |
| 51 | B | A | C |

It is thus apparent that the new phenylalanine derivatives exhibited an excellent α4β7-integrin inhibiting activity and also an excellent selectivity toward α4β1-integrin.

The new phenylalanine derivatives of the present invention have excellent α4β7-integrin inhibiting activity. Thus, the new phenylalanine derivatives of the present invention provide a therapeutic agent or preventive agent for diseases in which α4β7 integrin-depending adhesion process relates to the pathology, such as inflammatory bowel diseases, diabetes, tumor proliferation and tumor metastasis.

What is claimed is:

1. A phenylalanine derivative of formula (1) or a pharmaceutically acceptable salt thereof:

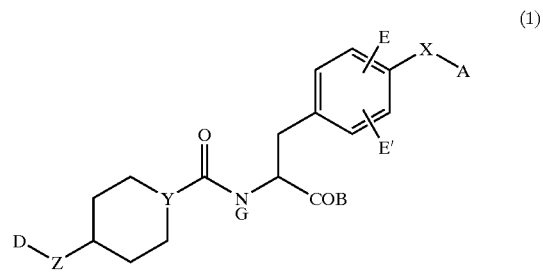

(1)

wherein X represents —O—, —O—SO$_2$—, —NR$^1$—, —NR$^1$—C(=O)—, —NR$^1$—SO$_2$—, —NR$^1$—C(=O)—NH—, —NR$^1$—C(=S)—NH— or —C(=O)—, wherein R$^1$ represents a hydrogen atom, a lower alkyl group, a lower alkenyl group, a lower alkynyl group, a lower alkyl group substituted with a cycloalkyl group which may contain a hetero atom(s) in the ring thereof, a lower alkyl group substituted with an aryl group or a lower alkyl group substituted with a heteroaryl group;

Y represents N or CH;

Z represents —C(=O)—, —S(=O)— or —SO$_2$—;

A represents a group of formula (2), a lower alkyl group, a lower alkenyl group, a lower alkynyl group, a cycloalkyl group which may contain a hetero atom(s) in the ring thereof, an aryl group, a heteroaryl group, a lower alkyl group substituted with a cycloalkyl group which may contain a hetero atom(s) in the ring thereof, a lower alkyl group substituted with a group of general formula (2), a lower alkyl group substituted with an aryl group, a lower alkyl group substituted with a heteroaryl group, a lower alkenyl group substituted with a cycloalkyl group which may contain a hetero atom(s) in the ring thereof, a lower alkenyl group substituted with an aryl group, a lower alkenyl group substituted with a heteroaryl group, a lower alkynyl group substituted with a cycloalkyl group which may contain a hetero atom(s) in the ring thereof, a lower alkynyl group substituted with an aryl group or a lower alkynyl group substituted with a heteroaryl group:

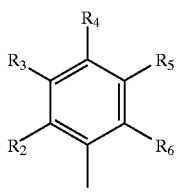

(2)

wherein $R^2$, $R^3$, $R^4$, $R^5$ and $R^6$ may be the same or different from one another, and each represents a hydrogen atom, a halogen atom, a hydroxyl group, a lower alkyl group, a lower alkenyl group, a lower alkynyl group, a cycloalkyl group which may contain a hetero atom(s) in the ring thereof, an aryl group, a heteroaryl group, a lower alkyl group substituted with a cycloalkyl group which may contain a hetero atom(s) in the ring thereof, a lower alkyl group substituted with an aryl group, a lower alkyl group substituted with a heteroaryl group, a lower alkoxyl group, a lower alkoxyl group substituted with a cycloalkyl group which may contain a hetero atom(s) in the ring thereof, a lower alkoxyl group substituted with an aryl group, a lower alkoxyl group substituted with a heteroaryl group, a cycloalkyloxy group which may contain a hetero atom(s) in the ring thereof, an aryloxy group, a heteroaryloxy group, a hydroxy-lower alkyl group, a hydroxy-lower alkenyl group, a hydroxy-lower alkoxyl group, a halogeno-lower alkyl group, a halogeno-lower alkoxyl group, a halogeno-lower alkenyl group, a nitro group, a cyano group, a substituted or unsubstituted amino group, a carboxyl group, a lower alkyloxycarbonyl group, a substituted or unsubstituted carbamoyl group, a lower alkanoyl group, an aroyl group, a lower alkylthio group, a lower alkylsulfonyl group or a substituted or unsubstituted sulfamoyl group;

B represents a hydroxyl group, a lower alkoxyl group or hydroxyamino group;

G represents a hydrogen atom, a lower alkyl group, a lower alkenyl group, a lower alkynyl group, a lower alkyl group substituted with a cycloalkyl group which may contain a hetero atom(s) in the ring thereof, a lower alkyl group substituted with an aryl group or a lower alkyl group substituted with a heteroaryl group;

D represents $OR^7$, $NR^7R^8$, $NHNR^7R^8$, $NR^7NHR^8$, $SR^7$ or $R^7$, wherein $R^7$ and $R^8$ may be the same or different from each other and each represents a hydrogen atom, a lower alkyl group, a lower alkenyl group, a lower alkynyl group, a cycloalkyl group which may contain a hetero atom(s) in the ring thereof, an aryl group, a heteroaryl group, a lower alkyl group substituted with a cycloalkyl group which may contain a hetero atom(s) in the ring thereof, a lower alkyl group substituted with an aryl group, a lower alkyl group substituted with a heteroaryl group, a lower alkenyl group substituted with a cycloalkyl group which may contain a hetero atom(s) in the ring thereof, a lower alkenyl group substituted with an aryl group, a lower alkenyl group substituted with a heteroaryl group, a lower alkynyl group substituted with a cycloalkyl group which may contain a hetero atom(s) in the ring thereof, a lower alkynyl group substituted with an aryl group, a lower alkynyl group substituted with a heteroaryl group, a halogeno-lower alkyl group, a halogeno-lower alkenyl group, a hydroxy-lower alkyl group, a hydroxy-lower alkenyl group or a substituted or unsubstituted amino-lower alkyl group, or $R^7$ and $R^8$ may be bonded together to form a ring which may contain one or two oxygen, nitrogen or sulfur atoms; and the substituent of the ring is a hydrogen atom, a halogen atom, hydroxyl group, a lower alkyl group, a lower alkenyl group, a lower alkynyl group, a cycloalkyl group which may contain a hetero atom(s) in the ring thereof, an aryl group, a heteroaryl group, a lower alkyl group substituted with a cycloalkyl group which may contain a hetero atom(s) in the ring thereof, a lower alkyl group substituted with an aryl group, a lower alkyl group substituted with a heteroaryl group, a lower alkanoyl group, an aroyl group, a halogeno-lower alkanoyl group, a lower alkyloxy group, nitro group, cyano group, a substituted or unsubstituted amino group, carboxyl group, a lower alkoxycarbonyl group, a substituted or unsubstituted carbamoyl group, a lower alkylthio group, a lower alkylsulfonyl group or a substituted or unsubstituted sulfamoyl group; and E and E' may be the same or different from each other and each represents a hydrogen atom, a halogen atom, a lower alkyl group, a lower alkyloxy group or nitro group.

2. The phenylalanine derivative or pharmaceutically acceptable salt thereof according to claim 1, wherein X is any of —O—, —O—SO$_2$—, —NR$^1$—, —NR$^1$—C(=O)—, —NR$^1$—SO$_2$—, —NR$^1$—C(=O)—NH— and —NR$^1$—C(=S)—NH—.

3. The phenylalanine derivative or pharmaceutically acceptable salt thereof according to claim 2, wherein D is any of NR$^7$R$^8$, NHNR$^7$R$^8$, NR$^7$NHR$^8$ and SR$^7$.

4. The phenylalanine derivative or pharmaceutically acceptable salt thereof according to claim 1, wherein:

X is any of —O—, —O—SO$_2$—, —NR$^1$—, —NR$^1$—C(=O)— and —NR$^1$—SO$_2$—;

Y is a group of the formula: CH;

Z is a group of the formula: —C(=O)—;

A is a group of formula (2), a lower alkyl group, a lower alkenyl group, a lower alkynyl group, a cycloalkyl group which may contain a hetero atom(s) in the ring thereof, an aryl group, a heteroaryl group, a lower alkyl group substituted with a cycloalkyl group which may contain a hetero atom(s) in the ring thereof, a lower alkyl group substituted with a group of formula (2), a lower alkyl group substituted with an aryl group or a lower alkyl group substituted with a heteroaryl group;

B is a hydroxyl group or a lower alkoxyl group; and

G is a hydrogen atom or a lower alkyl group.

5. The phenylalanine derivative or pharmaceutically acceptable salt thereof according to claim 1, wherein:

X is —O—;

Y is a group of the formula: CH;

Z is a group of the formula: —C(=O)—;

A is a lower alkyl group substituted with a group of formula (2), $R^2$, $R^3$, $R^4$, $R^5$ and $R^6$ may be the same or different from one another, and each represents a hydrogen atom or a halogen atom;

B is a hydroxyl group;

G is a hydrogen atom;

D is $OR^7$, $NR^7R^8$ or $NHNR^7R^8$,

R$^7$ and R$^8$ may be the same or different from each other and each represents a hydrogen atom, a lower alkyl group, a cycloalkyl group which may contain a hetero atom(s) in the ring thereof, an aryl group, a heteroaryl group, a lower alkyl group substituted with a cycloalkyl group which may contain a hetero atom(s) in the ring thereof, a lower alkyl group substituted with an aryl group or a lower alkyl group substituted with a heteroaryl group, or R$^7$ and R$^8$ may be bonded together to form a ring which may contain one or two oxygen, nitrogen or sulfur atoms; and the substituent of the ring is a hydrogen atom, a halogen atom, a hydroxyl group, a lower alkyl group, a lower alkenyl group, a lower alkynyl group, a cycloalkyl group which may contain a hetero atom(s) in the ring thereof, an aryl group, a heteroaryl group, a lower alkyl group substituted with a cycloalkyl group which may contain a hetero atom(s) in the ring thereof, a lower alkyl group substituted with an aryl group, a lower alkyl group substituted with a heteroaryl group, a lower alkanoyl group, an aroyl group, a halogeno-lower alkanoyl group, a lower alkyloxy group, nitro group, cyano group, a substituted or unsubstituted amino group, carboxyl group, a lower alkyloxycarbonyl group, a substituted or unsubstituted carbamoyl group, a lower alkylthio group, a lower alkylsulfonyl group or a substituted or unsubstituted sulfamoyl group; and E and E' each represents a hydrogen atom.

6. The phenylalanine derivative or pharmaceutically acceptable salt thereof according to claim 1, wherein:

X is —O—;

Y is a group of the formula: CH;

Z is a group of the formula: —C(=O)—;

A is a lower alkyl group substituted with a group of formula (2),

R$^2$, R$^3$, R$^4$, R$^5$ and R$^6$ may be the same or different from one another, and each represents a hydrogen atom or a halogen atom;

B is a hydroxyl group or a lower alkoxyl group;

G is a hydrogen atom;

D is $NR^7R^8$ or $NHNR^7R^8$,

R$^7$ and R$^8$ may be the same or different from each other and each represents a hydrogen atom, a lower alkyl group, a cycloalkyl group which may contain a hetero atom(s) in the ring thereof, an aryl group, a heteroaryl group, a lower alkyl group substituted with a cycloalkyl group which may contain a hetero atom(s) in the ring thereof, a lower alkyl group substituted with an aryl group or a lower alkyl group substituted with a heteroaryl group, or R$^7$ and R$^8$ may be bonded together to form a ring which may contain one or two oxygen, nitrogen or sulfur atoms; and the substituent of the ring is a hydrogen atom, a halogen atom, hydroxyl group, a lower alkyl group, a lower alkenyl group, a lower alkynyl group, a cycloalkyl group which may contain a hetero atom(s) in the ring thereof, an aryl group, a heteroaryl group, a lower alkyl group substituted with a cycloalkyl group which may contain a hetero atom(s) in the ring thereof, a lower alkyl group substituted with an aryl group, a lower alkyl group substituted with a heteroaryl group, a lower alkanoyl group, an aroyl group, a halogeno-lower alkanoyl group, a lower alkyloxy group, nitro group, cyano group, a substituted or unsubstituted amino group, carboxyl group, a lower alkyloxycarbonyl group, a substituted or unsubstituted carbamoyl group, a lower alkylthio group, a lower alkylsulfonyl group or a substituted or unsubstituted sulfamoyl group; and E and E' each represent hydrogen atom.

7. The phenylalanine derivative or pharmaceutically acceptable salt thereof according to claim 1, wherein:

X is a group of the formula: —NR$_1$—C(=O);

Y is a group of the formula: CH;

Z is a group of the formula: —C(=O)—;

A is a heteroaryl group;

B is a hydroxyl group or a lower alkoxyl group;

G is a hydrogen atom;

D is $NR^7R^8$ or $NHNR^7R^8$,

R$^7$ and R$^8$ may be the same or different from each other and each represents a hydrogen atom, a lower alkyl group, a cycloalkyl group which may contain a hetero atom(s) in the ring thereof, an aryl group, a heteroaryl group, a lower alkyl group substituted with a cycloalkyl group which may contain a hetero atom(s) in the ring thereof, a lower alkyl group substituted with an aryl group or a lower alkyl group substituted with a heteroaryl group, or R$^7$ and R$^8$ may be bonded together to form a ring which may contain one or two oxygen, nitrogen or sulfur atoms; and the substituent of the ring is hydrogen atom, a halogen atom, hydroxyl group, a lower alkyl group, a lower alkenyl group, a lower alkynyl group, a cycloalkyl group which may contain a hetero atom(s) in the ring thereof, an aryl group, a heteroaryl group, a lower alkyl group substituted with a cycloalkyl group which may contain a hetero atom(s) in the ring thereof, a lower alkyl group substituted with an aryl group, a lower alkyl group substituted with a heteroaryl group, a lower alkanoyl group, an aroyl group, a halogeno-lower alkanoyl group, a lower alkyloxy group, nitro group, cyano group, a substituted or unsubstituted amino group, carboxyl group, a lower alkyloxycarbonyl group, a substituted or unsubstituted carbamoyl group, a lower alkylthio group, a lower alkylsulfonyl group or a substituted or unsubstituted sulfamoyl group; and E and E' each represents a hydrogen atom.

8. The phenylalanine derivative or pharmaceutically acceptable salt thereof according to claim 1 selected from the group consisting of N-(trans-4-carboxycyclohexane-1-carbonyl)-O-(2,6-dichlorobenzyl)-L-tyrosine;

N-(trans-4-phenylhydrazinocarbonylcyclohexane-1-carbonyl)-O-(2,6-dichlorobenzyl)-L-tyrosine; and N-[trans-4-(4-bromophenylhydrazinocarbonyl) cyclohexane-1-carbonyl]-O-(2,6-dichlorobenzyl)-L-tyrosine.

9. The phenylalanine derivative or pharmaceutically acceptable salt thereof according to claim 1 selected from the group consisting of

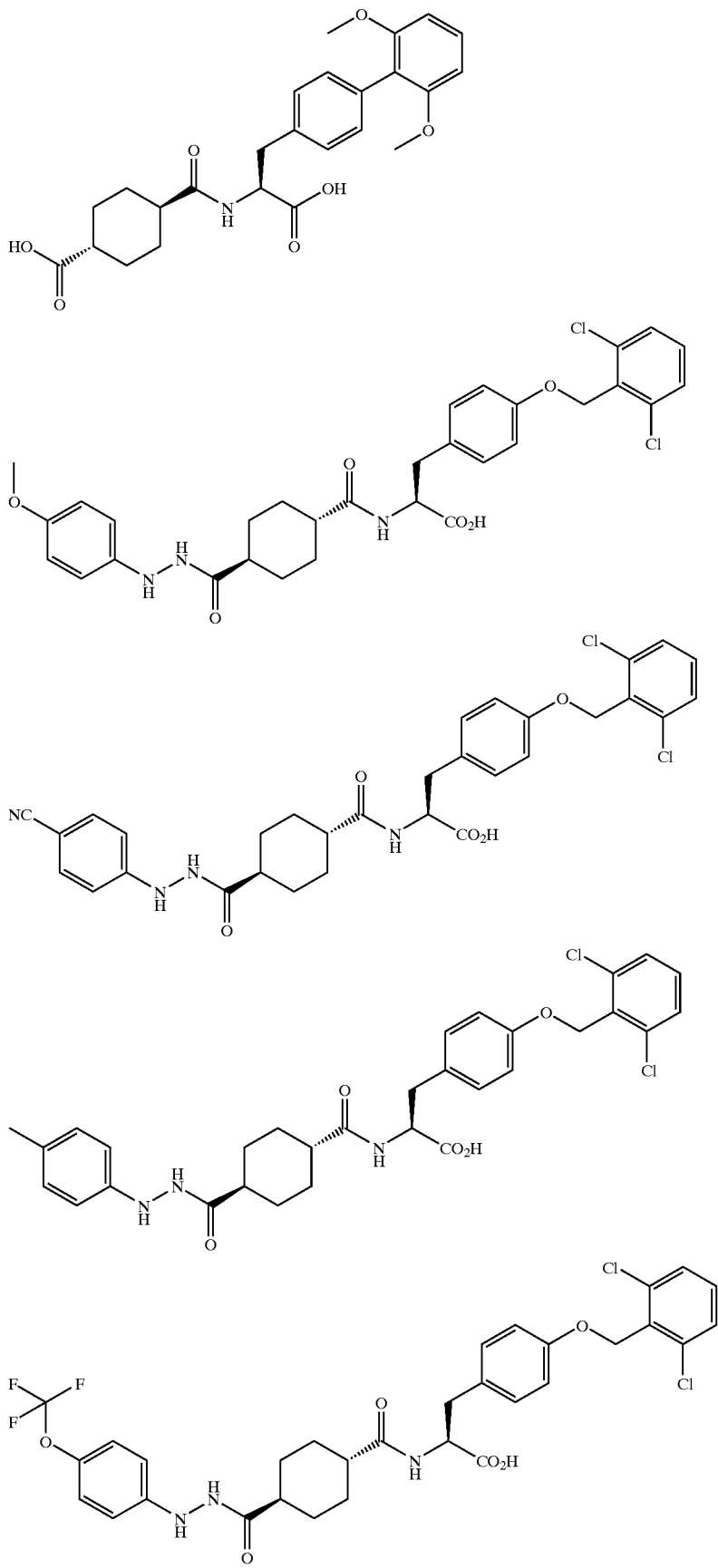

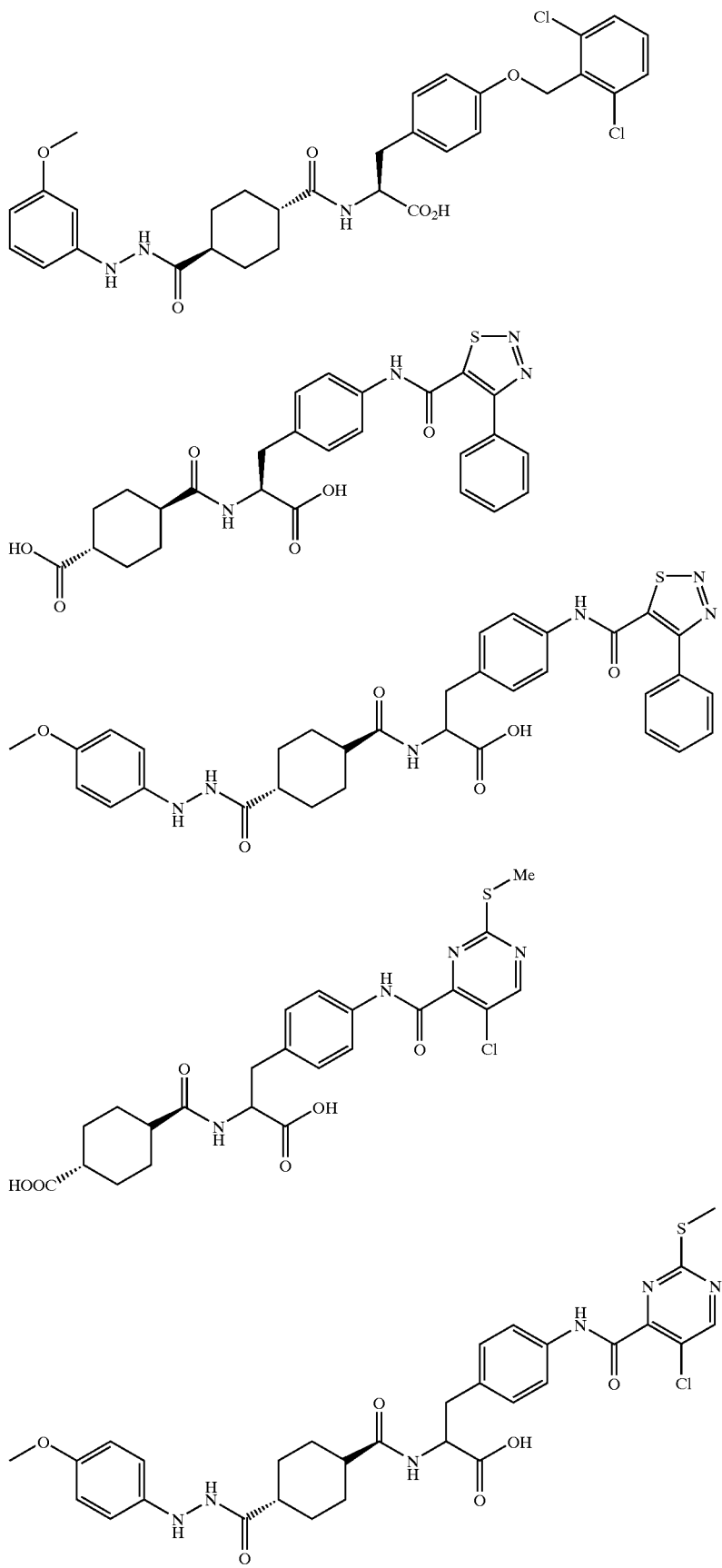

-continued

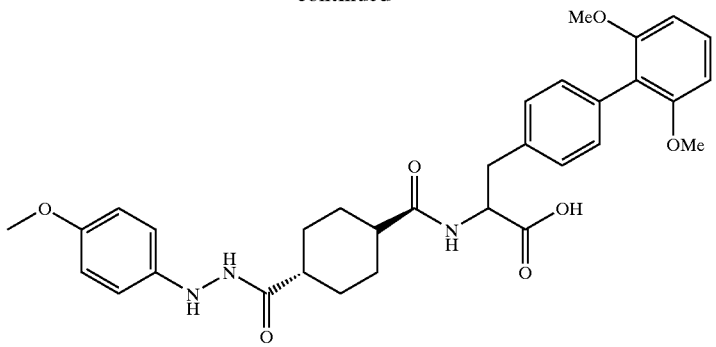

10. An antagonist to α4β7 integrin, which comprises the phenylalanine derivative or pharmaceutically acceptable salt thereof according to claim 1.

11. An antagonist to α4β7 integrin, which comprises the phenylalanine derivative or pharmaceutically acceptable salt thereof according to claim 8.

12. An antagonist to α4β7 integrin, which comprises the phenylalanine derivative or pharmaceutically acceptable salt thereof according to claim 9.

13. A method for treating or preventing a disease in which α4β7 integrin-depending adhesion process relates to the pathology, which comprises administering an effective amount of a phenylalanine derivative or pharmaceutically acceptable salt thereof according to claim 1 to a subject in need thereof.

14. A method for treating or preventing a disease in which α4β7 integrin-depending adhesion process relates to the pathology, which comprises administering an effective amount of a phenylalanine derivative or pharmaceutically acceptable salt thereof according to claim 8 to a subject in need thereof.

15. A method for treating or preventing a disease in which α4β7 integrin-depending adhesion process relates to the pathology, which comprises administering an effective amount of a phenylalanine derivative or pharmaceutically acceptable salt thereof according to claim 9 to a subject in need thereof.

16. A method for treating or preventing inflammatory intestinal diseases, diabetes, tumor proliferation or tumor metastasis, which comprises administering an effective amount of a phenylalanine derivative or pharmaceutically acceptable salt thereof according to claim 1 to a subject in need thereof.

17. A method for treating or preventing inflammatory intestinal diseases, diabetes, tumor proliferation or tumor metastasis, which comprises administering an effective amount of a phenylalanine derivative or pharmaceutically acceptable salt thereof according to claim 8 to a subject in need thereof.

18. A method for treating or preventing inflammatory intestinal diseases, diabetes, tumor proliferation or tumor metastasis, which comprises administering an effective amount of a phenylalanine derivative or pharmaceutically acceptable salt thereof according to claim 9 to a subject in need thereof.

19. A pharmaceutical composition comprising the phenylalanine derivative or pharmaceutically acceptable salt thereof according to claim 1.

20. A pharmaceutical composition comprising the phenylalanine derivative or pharmaceutically acceptable salt thereof according to claim 8.

21. A pharmaceutical composition comprising the phenylalanine derivative or pharmaceutically acceptable salt thereof according to claim 9.

22. The phenylalanine derivative or pharmaceutically acceptable salt thereof according to claim 1, wherein X represents —O—, and A represents a lower alkyl group substituted with a group of formula (2).

23. The phenylalanine derivative or pharmaceutically acceptable salt thereof according to claim 1, wherein X represents —NR$^1$—C(=O)—, and A represents a group of formula (2), an aryl group, or a heteroaryl group.

24. The phenylalanine derivative or pharmaceutically acceptable salt thereof according to claim 1, wherein X represents —NR$^1$—SO$_2$—, and A represents a group of formula (2), an aryl group, or a heteroaryl group.

25. The phenylalanine derivative or pharmaceutically acceptable salt thereof according to claim 1, wherein X represents —C(=O)—, and A represents a group of formula (2), an aryl group, or a heteroaryl group.

26. A method for treating or preventing a disease in which α4β7 integrin-depending adhesion process relates to the pathology, which comprises administering an effective amount of a phenylalanine derivative or pharmaceutically acceptable salt thereof according to claim 23 to a subject in need thereof.

27. A method for treating or preventing inflammatory intestinal diseases, diabetes, tumor proliferation or tumor metastasis, which comprises administering an effective amount of a phenylalanine derivative or pharmaceutically acceptable salt thereof according to claim 23 to a subject in need thereof.

28. A phenylalanine derivative of formula (1) or a pharmaceutically acceptable salt thereof:

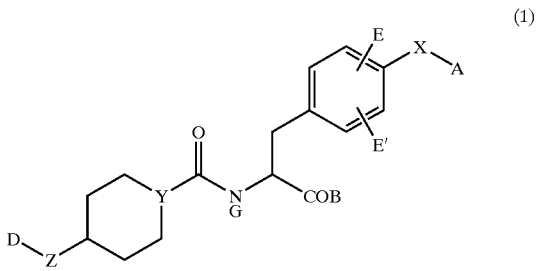

wherein X represents an interatomic bond;
Y represents N or CH;
Z represents —C(=O)—, —S(=O)— or —SO$_2$—;
A represents an aryl group or a heteroaryl group;
B represents a hydroxyl group, a lower alkoxyl group or hydroxyamino group;

G represents a hydrogen atom, a lower alkyl group, a lower alkenyl group, a lower alkynyl group, a lower alkyl group substituted with a cycloalkyl group which may contain a hetero atom(s) in the ring thereof, a lower alkyl group substituted with an aryl group or a lower alkyl group substituted with a heteroaryl group;

D represents $OR^7$, $NR^7R^8$, $NHNR^7R^8$, $NR^7NHR^8$, $SR^7$ or $R^7$, wherein $R^7$ and $R^8$ may be the same or different from each other and each represents a hydrogen atom, a lower alkyl group, a lower alkenyl group, a lower alkynyl group, a cycloalkyl group which may contain a hetero atom(s) in the ring thereof, an aryl group, a heteroaryl group, a lower alkyl group substituted with a cycloalkyl group which may contain a hetero atom(s) in the ring thereof, a lower alkyl group substituted with an aryl group, a lower alkyl group substituted with a heteroaryl group, a lower alkenyl group substituted with a cycloalkyl group which may contain a hetero atom(s) in the ring thereof, a lower alkenyl group substituted with an aryl group, a lower alkenyl group substituted with a heteroaryl group, a lower alkynyl group substituted with a cycloalkyl group which may contain a hetero atom(s) in the ring thereof, a lower alkynyl group substituted with an aryl group, a lower alkynyl group substituted with a heteroaryl group, a halogeno-lower alkyl group, a halogeno-lower alkenyl group, a hydroxy-lower alkyl group, a hydroxy-lower alkenyl group or a substituted or unsubstituted amino-lower alkyl group, or $R^7$ and $R^8$ may be bonded together to form a ring which may contain one or two oxygen, nitrogen or sulfur, atoms; and the substituent of the ring is a hydrogen atom, a halogen atom, hydroxyl group, a lower alkyl group, a lower alkenyl group, a lower alkynyl group, a cycloalkyl group which may contain a hetero atom(s) in the ring thereof, an aryl group, a heteroaryl group, a lower alkyl group substituted with a cycloalkyl group which may contain a hetero atom(s) in the ring thereof, a lower alkyl group substituted with an aryl group, a lower alkyl group substituted with a heteroaryl group, a lower alkanoyl group, an aroyl group, a halogeno-lower alkanoyl group, a lower alkyloxy group, nitro group, cyano group, a substituted or unsubstituted amino group, carboxyl group, a lower alkoxycarbonyl group, a substituted or unsubstituted carbamoyl group, a lower alkylthio group, a lower alkylsulfonyl group or a substituted or unsubstituted sulfamoyl group; and E and E' may be the same or different from each other and each represents a hydrogen atom, a halogen atom, a lower alkyl group, a lower alkyloxy group or nitro group, provided that when Y represents N, D represents $NR^7R^8$, $NHNR^7R^8$, $NR^7NHR^8$ or $SR^7$.

29. An antagonist to α4β7 integrin, which comprises the phenylalanine derivative or pharmaceutically acceptable salt thereof according to claim 28.

30. The phenylalanine derivative or pharmaceutically acceptable salt thereof according to claim 28, wherein:

X is an interatomic bond;

Y is a group of the formula: CH;

Z is a group of the formula: —C(=O)—;

A is a group of formula (2),

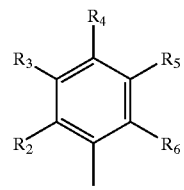

(2)

$R^2$, $R^3$, $R^4$, $R^5$ and $R^6$ may be the same or different from one another, and each represents a hydrogen atom or a halogen atom;

B is a hydroxyl group or a lower alkoxyl group;

G is a hydrogen atom;

D is $NR^7R^8$ or $NHNR^7R^8$, wherein $R^7$ and $R^8$ may be the same or different from each other and each represents a hydrogen atom, a lower alkyl group, a cycloalkyl group which may contain a hetero atom(s) in the ring thereof, an aryl group, a heteroaryl group, a lower alkyl group substituted with a cycloalkyl group which may contain a hetero atom(s) in the ring thereof, a lower alkyl group substituted with an aryl group or a lower alkyl group substituted with a heteroaryl group, or $R^7$ and $R^8$ may be bonded together to form a ring which may contain one or two oxygen, nitrogen or sulfur atoms; and the substituent of the ring is a hydrogen atom, a halogen atom, a hydroxyl group, a lower alkyl group, a lower alkenyl group, a lower alkynyl group, a cycloalkyl group which may contain a hetero atom(s) in the ring thereof, an aryl group, a heteroaryl group, a lower alkyl group substituted with a cycloalkyl group which may contain a hetero atom(s) in the ring thereof, a lower alkyl group substituted with an aryl group, a lower alkyl group substituted with a heteroaryl group, a lower alkanoyl group, an aroyl group, a halogeno-lower alkanoyl group, a lower alkyloxy group, nitro group, cyano group, a substituted or unsubstituted amino group, carboxyl group, a lower alkyloxycarbonyl group, a substituted or unsubstituted carbamoyl group, a lower alkylthio group, a lower alkylsulfonyl group or a substituted or unsubstituted sulfamoyl group; and E and E' each represents a hydrogen atom.

31. A pharmaceutical composition comprising the phenylalanine derivative or pharmaceutically acceptable salt thereof according to claim 28.

* * * * *